(12) United States Patent
Khabar

(10) Patent No.: US 8,790,896 B2
(45) Date of Patent: Jul. 29, 2014

(54) METHOD FOR INCREASING PROTEIN EXPRESSION IN CELLS

(75) Inventor: Khalid S. Khabar, Riyadh (SA)

(73) Assignees: King Faisal Specialist Hospital & Research Centre, Riyadh (SA); Terramark Markencreation GmbH, Bremen (DE)

( * ) Notice: Subject to any disclaimer, the term of this patent is extended or adjusted under 35 U.S.C. 154(b) by 396 days.

(21) Appl. No.: 13/144,621

(22) PCT Filed: Jan. 19, 2010

(86) PCT No.: PCT/EP2010/000271
§ 371 (c)(1),
(2), (4) Date: Sep. 3, 2011

(87) PCT Pub. No.: WO2010/081741
PCT Pub. Date: Jul. 22, 2010

(65) Prior Publication Data
US 2011/0306753 A1    Dec. 15, 2011

(30) Foreign Application Priority Data
Jan. 19, 2009    (WO) ................. PCT/EP2009/000302

(51) Int. Cl.
*C12P 21/02*    (2006.01)
(52) U.S. Cl.
USPC .......... 435/69.1; 435/462; 435/463; 530/350; 530/351; 530/387.1; 536/23.4; 536/24.1
(58) Field of Classification Search
None
See application file for complete search history.

(56) References Cited

PUBLICATIONS

Chandrasekaran et al., "RNase-L regulates the stability of mitochondrial DNA-encoded mRNAs in mouse embryo fibroblasts," Biochemical and Biophysical Research Communications, 2004, vol. 321, No. 1, pp. 18-23.
Han et al., "Sensitivity of hepatitis C virus RNA to the antiviral enzyme ribonuclease L is determined by a subset of efficient cleavage sites," Journal of Interferon and Cytokine Research, 2004, vol. 24, No. 11, pp. 664-676.
Khabar et al., "RNase L mediates transient control of the interferon response through modulation of the double-stranded RNA-dependent protein kinase PKR," Journal of Biological Chemistry, 2003, vol. 278, No. 22 pp. 20124-20132.
Khabar et al., "Post-transcriptional control of the interferon system," Biochimie, 2007, vol. 89 No. 6-7, pp. 761-769.
Li et al., "RNase-L-dependent destabilization of interferon-induced mRNAs: A role for the 2-5A system in attenuation of the interferon response," Journal of Biological Chemistry, 2000, vol. 275, No. 12, pp. 8880-8888.
Wreschner et al., "Interferon action-sequence sensitivity of the ppp(A2'p)$_n$A-dependent ribonuclease" Nature, 1981, vol. 289, No. 29, pp. 414-417.

*Primary Examiner* — Jim Ketter
(74) *Attorney, Agent, or Firm* — Saliwanchik, Lloyd & Eisenschenk

(57) ABSTRACT

The present invention relates to a method for increasing the expression of a protein in cells, preferably in eukaryotic cells, by reducing the number of RNase L cleavage sites in the coding and/or non-coding region of the nucleic acid sequence of said protein. Furthermore, it relates to nucleic acid sequences exhibiting a reduced number of RNase L cleavage sites as well as to the proteins translated from such sequences.

15 Claims, 7 Drawing Sheets

EXAMPLES OF REPORTERS: PERFORMANCE

Hek 293 cells were transfected with wild type or modified firefly luciferase expression vector. Luciferase activity levels were quantified by a luminometer. There was 5 and 100 fold difference in two independent experiments.

Huh7 cells were transfected with different pcr products generated from the wild type or modified firefly luciferase expression vector. luciferase activity levels were quantified by a luminometer. There was 20-100 fold difference in two independent experiments.

EXAMPLES OF THERAPEUTIC PROTEINS, ANTIBODIES, AND VACCINES:

Hek cells were transfected with wild type of modified hepatitis b surface antigen expression vector. The protein was quantified as miu/ml. there was approximately 4-fold difference. The assay is not quantitative, thus, the fold difference can be higher.

METHOD FOR INCREASING PROTEIN EXPRESSION IN CELLS

CROSS REFERENCE TO A RELATED APPLICATION

This application is a National Stage Application of International Application Number PCT/EP2010/000271, filed Jan. 19, 2010; which claims priority to International Application PCT/EP2009/000302, filed on Jan. 19, 2009; all of which are incorporated herein by reference in their entirety.

The Sequence Listing for this application is labeled "Asfiled_ST25.txt", which was created on Jul. 14, 2011, and is 40 KB. The entire contents are incorporated herein by reference in their entirety.

The present invention relates to a method for increasing the expression of a protein in cells, preferably in eukaryotic cells by reducing the number of RNase L cleavage sites in the coding and/or non-coding region of the nucleic acid sequence of said protein. Furthermore, it relates to nucleic acid sequences exhibiting a reduced number of RNase L cleavage sites as well as to the proteins translated from such sequences.

Transient response genes regulate critical biological responses that include cell proliferation, signal transduction events, and responses to exogenous agents, such as inflammatory stimuli, microbes, and radiation (Lai et al., 2006; Lal et al., 2004; Lopez de Silanes et al., 2005). They are controlled by both cis-acting factors such as specific sequence elements and trans-acting factors like certain RNA binding proteins. Sequence elements, mainly in the 3' untranslated region (3'UTR) and modulation by RNA binding proteins can affect messenger RNA (mRNA) stability and protein translation.

An appreciable number of genes harbor destabilizing sequence elements in the 3' UTR of their mRNA, mostly adenylate-uridylate (AU)-rich elements (AREs). These AREs comprise a heterogeneous group of sequence classes that can affect protein interactions with the mRNA, and therefore influence the mRNA decay characteristics (Bakheet et al., 2006; Barreau et al., 2005). The stabilization of cellular mRNAs can occur by the activity of mRNA stabilization-promoting proteins, such as the HuR protein, or by inactivation of RNA decay promoting proteins, such as the zinc finger protein tristetraprolin (TTP).

A different class of trans-acting factors that can affect cellular mRNAs is the endoribonuclease Ribonuclease L (RNase L), which is an ubiquitous intracellular enzyme that has previously been thought to be specific to viral mRNAs. However, recent studies showed that RNase L can also participate in the transient response of certain biological processes (Khabar et al., 2003a; Li et al., 2000). RNase L is considered to be a part of the interferon (IFN) system. IFN induces gene expression of the enzyme oligoadenylate synthetase (OAS) which, upon binding to viral double-stranded RNA intermediates, becomes activated and synthesizes short 2'-5'oligoadenylates (2-5A). These, in turn, activate RNase L, which potently degrades viral mRNAs. RNase L is activated by subnanomolar levels of 2-5A, resulting in the cleavage of single-stranded regions of viral RNA, preferentially after UU and UA dinucleotides in viral mRNAs (Wrechester et al., 1981; Han et al., 2004). At higher levels, RNase L may lead to broader effects such as cleavage of 18 S and 28 S ribosomal RNAs (Wreschner et al., 1981).

In recent years it has become widely accepted that RNase L participates in the degradation of selected cellular mRNAs (Bisbal et al., 2000; Chandrasekaran et al., 2004; Khabar et al., 2003b; Le Roy et al., 2001; Li et al., 2000). Specifically, RNase L has been shown to down-regulate PKR mRNA (Khabar et al., 2003b). During the IFN antiviral response in normal cells, PKR mRNA expression is transient, but in RNase L-null cells, extended kinetics of PKR mRNA expression is observed due to increased mRNA stability (Khabar et al., 2003b). The effect results in prolongation of the PKR-dependent phosphorylation of the subunit of eukaryotic translation initiation factor 2, eIF2α, a process that leads to inhibition of viral protein synthesis (Khabar et al., 2003b). Thus, RNase L contributes to the transient nature of the IFN response in order to ensure a brief translational arrest imparted by PKR. A similar role of RNase L negative regulation of the IFN response has also been suggested by the report that a novel IFN-stimulated gene encoding a 43-kDa ubiquitin-specific protease, designated ISG43, is down-regulated by RNase L (Li et al., 2000). This regulation occurs at the level of mRNA stability, since the ISG43 mRNA half life increases in RNase L-null cells (Li et al., 2000). RNase L can down-regulate another functionally important cellular mRNA, myoD, encoding an import transcription factor essential for muscle differentiation. RNase L and its inhibitor RLI are sequentially induced during C2 cell line myoblast differentiation to myotubes (Bisbal et al., 2000). Inhibition or over-expression of RNase L prolongs or decreases MyoD mRNA half life, respectively (Bisbal et al., 2000). Since a pool of RNase L molecules localizes to mitochondria and is increased following IFN-α treatment, a role of RNase L in down-regulating mitochondrial mRNAs, such as those of CYTB, ATPase 6 (ATP6), and cytochrome oxidase II (CO), has been proposed as a mechanism of the anti-proliferative action of IFN (Le Roy et al., 2001). This was demonstrated by reducing RNase L activity through the introduction of an antisense construct or by directly activating RNase L activity by 2-5A (Le Roy et al., 2001). It has further been shown that RNase L exhibits a preference for viral mRNA, for example encephalomyocarditits virus (EMCV), when compared to non-viral mRNAs, particularly in conditions where the levels of 2-5A is limiting. (Li et al., 1998a). The effects of RNase L on cellular mRNAs appear to be highly restricted to specific mRNAs, since no global effects on cellular mRNAs are observed in the studies that have dealt with this topic. Furthermore, none of the above studies demonstrates a direct binding of RNase L to cellular target mRNAs or a sequence specificity as shown for viral mRNAs. Thus, the mechanism of RNase L activity in connection with non-viral cellular mRNAs remains largely unclear.

Dominant negative forms of RNase L have previously been generated by either amino acid substitutions or by truncation of the full length protein. For example, a dominant negative RNase L, ZB1, inhibits the antiviral and anti-proliferative action of wild type RNase L; it is a truncated form of murine RNase L, which lacks 89 carboxy-terminal amino acids (Hassel et al., 1993). Dong et al., 2001 describe other truncations and point mutations of RNase L, e.g. mutations in the nuclease domain (R667A).

U.S. Pat. No. 6,762,038 suggests the use of mutant embryonic fibroblasts cell lines (MEFs) generated from mice having a homozygous disruption in their RNase L gene (Zhou et al., 1997) for enhanced expression of transfected genes. However, the effect of enhanced expression is restricted to these particular cell lines. Furthermore, the creation of new RNase L-null cell lines is a very laborious process and not readily applicable to all mammalian and/or eukaryotic expression systems.

Mammalian expression systems have become an important means for therapeutic protein and antibody production and possess several advantages over prokaryotic expression systems, e.g. with respect to proper protein folding and post-translational modifications, such as glycolysation. However, in many systems, low protein expression yields represent a costly technical obstacle. This is particularly problematic, if the desired protein is inherently difficult to express, e.g. membrane proteins, such as G-protein linked receptors (GPCRs), large proteins, antibodies, fusion proteins, protein complexes, vaccines, and blood plasma proteins. Reasons for this difficulty could be an inherent instability of the protein itself, an inherent instability of the mRNA, as it is the case for AU-rich elements containing mRNAs, or weak promoter activity.

Common solutions to these problems focused on increasing the expression of proteins by providing strong promoters, such as the CMV promoter, and enhancer elements upstream or downstream of the promoter including specific types of introns, such as intron A of CMV. Other solutions involved chromatin Matrix Attachment Region (MAR) elements which are 300-3000 base pairs long DNA elements that are important in nuclear and chromosomal architecture. It was proposed that these elements prevent the neighbouring chromatin from affecting transgene expression, which leads to an increased probability of isolating a clone exhibiting the desired regulated expression (U.S. Pat. No. 7,129,062). This particular approach is potentially problematic as it may involve several different vector constructs to achieve the effect. Despite the availability of these approaches, there is still a need to further increase the protein expression of proteins that are difficult to express, such as those mentioned above.

Codon optimization (or codon usage optimization) is another method known in the art to boost protein production. It is based on the observation that, if a nucleic acid sequence encoding the protein to be expressed contains codons (triplets) that are rarely used by the host, its expression level will not be maximal. Codon optimization basically involves altering the rare codons in the target nucleic acid sequence, so that they more closely reflect the codon usage of the host. The information usually used for the optimization process is therefore the DNA or protein sequence to be optimized and a codon usage table of the respective host (see for example Table 1 for the human genome). The codon usage table lists the relative frequency of each possible codon for a particular amino acid in a given organism. A full list of codon usage bias in all organisms is found on the website: http://www.kazusa.or.jp/codon/. Several web-based programs are also available to optimize codons based on codon usage bias for a given host organism. Codon optimization may be successful in some situations where genes of non-human or non-mammalian origin are expressed in human or other mammalian host cells, and vice versa. However, codon usage is just one of many factors influencing the expression level of a protein, and the effect of codon optimization is often limited.

It was an object of the present invention to provide for a method to significantly improve the yield of endogenous and exogenous (recombinant) proteins expressed in cells of any organism, preferably in eukaryotic cells, including proteins that are inherently difficult to express. This method should be time and cost efficient and should allow for the large-scale production of proteins in cells of any type of organism including prokaryotic and eukaryotic cells. It was another object of the present invention to achieve this improvement in expression yields without changing regulatory approved features for the production of recombinant proteins, such as the cell lines used, recombinant protein characteristics, or the use of exogenous materials, in order to allow for the production of therapeutically used proteins.

The objects of the present invention are solved by a method for increasing the expression of a protein in cells, preferably eukaryotic cells, said method comprising the step of reducing the number of RNase L cleavage sites in the nucleic acid sequence of said protein. In one embodiment, said cells are prokaryotic cells; in another embodiment, said cells are eukaryotic cells.

The nucleic acid sequence of a protein comprises both coding and non-coding regions, i.e. regions that are translated into a sequence of amino acids (also referred to as exons) and regions that are not translated into a sequence of amino acids. Non-coding regions of the nucleic acid sequence are for example the 5' untranslated region (5'UTR), the 3' untranslated region (3'UTR), and introns. All of these elements (5'UTR, 3'UTR, introns, and the coding region) can control gene and protein expression, and are, thus, targets for the above method. According to the invention, said step of reducing the number of RNase L cleavage sites reduces said number either in the coding region or non-coding region, or in both.

In one embodiment said number of RNase L cleavage sites is reduced by at least 10%, preferably at least 25%, more preferably at least 50% (compared to the number of RNase L cleavage sites in the wild type nucleic acid sequence).

Preferably said cleavage sites are UU and/or UA dinucleotides.

RNase L is an endoribonuclease, and is, thus, only active on the RNA level (both primary RNA, i.e. unspliced, and mRNA, i.e. spliced). UU and UA dinucleotides only occur on the RNA level.

However, it is preferred that said step of reducing the number of RNase L cleavage sites in the nucleic acid sequence of said protein is performed on the DNA level: UU and UA dinucleotides in an RNA sequence correspond to TT and TA dinucleotides in a DNA sequence. Techniques that allow to specifically change a given DNA sequence are well know in the art and include, but are not limited to gene synthesis, site-directed mutagenesis, deletion mutations by restriction digestion, and mutation introduction by recombination. The technique of gene synthesis is particularly preferred according to the present invention.

In one embodiment of the present invention said step of reducing the number of RNase L cleavage sites reduces said number in the coding region of said nucleic acid sequence.

Preferably said step of reducing the number of RNase L cleavage sites in said nucleic acid sequence is performed without altering the amino acid sequence of said protein. The open reading frame (ORF) is, thus, not altered by said step.

In one embodiment in said step of reducing the number of RNase L cleavage sites a codon comprising a UU and/or UA dinucleotide is exchanged for an alternative codon not comprising a UU and/or UA dinucleotide and coding for the same amino acid.

In one embodiment in said step of reducing the number of RNase L cleavage sites at least one codon of an adjacent pair of codons comprising a UU and/or UA dinucleotide is exchanged for an alternative codon coding for the same amino acid so that said adjacent pair of codons does no longer comprise a UU and/or UA dinucleotide.

Preferably the first codon of said adjacent pair of codons comprising a UU and/or UA dinucleotide is exchanged.

In one embodiment said alternative codon is the more frequently used codon in said cells, preferably in said eukaryotic cells.

In one embodiment of the present invention said step of reducing the number of RNase L cleavage sites reduces said number in the non-coding region of said nucleic acid sequence.

Preferably said non-coding region is a 5'UTR, a 3'UTR, or an intron.

Examples for introns include, but are not limited to the CMV intron, SV40 intron, rabbit beta globin intron (RBTG), and synthetic introns.

In one embodiment said step of reducing the number of RNase L cleavage sites in the non-coding region of said nucleic acid sequence is performed by mutation, deletion, or insertion of nucleotides.

Preferably said step of reducing the number of RNase L cleavage sites in the non-coding region of said nucleic acid sequence does not alter functionally important elements in the non-coding region, such as sequences in the 5'UTR that are close to the initiation codon (ATG), since they may harbor translation enhancing sequences (e.g. kozac), the poly A signal in the 3'UTR (e.g. AAUAAA or AUUAAA) or other necessary or accessory sequence elements used for polyadenylation, intron-exon junctions/boundaries, splicing branch points and exon donor/acceptor splice sites in introns, and the CT-rich area between the splice acceptor site to the end of the branch point. For example there is an U-rich 50 nucleotide region that is downstream of the strong poly A signal, which should not be altered when possible (Legendre and Gautheret, 2003).

Preferably said step of reducing the number of RNase L cleavage sites in the non-coding region does not
(a) change the GC content of an intron to more than 80% and its length to less than 80%,
(b) change the GC content of a 5'UTR to more than 80%, and
(c) change the GC content of a 3'UTR to more than 80% and its length to less than 80%.

In one embodiment above method further comprises the step of codon optimization prior to said step of reducing the number of RNase L cleavage sites.

In one embodiment above method further comprises the step of transfecting said nucleic acid sequence of said protein into said cells, preferably into said eukaryotic cells in form of an expression active PCR product or contained in an expression vector after said step of reducing the number of RNase L cleavage sites.

The term "expression active PCR product" as used herein is meant to refer to a PCR product that is generated by PCR amplification using two primers complementary to sequences flanking the DNA sequence of interest, such as a cDNA, an open reading frame, or a gene that is contained in an expression vector, wherein the resulting PCR product contains a promoter, the DNA sequence of interest, and a termination sequence, and allows the expression of the DNA of interest, when transfected to a host cell (see also: Al-Zoghaibi et al., 2007).

According to the present invention any expression vector can be used, however, eukaryotic/mammalian expression vectors are preferable. Mammalian expression vectors are widespread tools to study the biological function of a protein, and various types (e.g. plasmid-based or viral-based vectors) are known in the art. Suitable expression vectors are not limited to a specific promoter, 5'UTR, 3'UTR, or intron. They can be constitutively expressed, inducible, repressed or regulatable.

According to the invention, it is preferred that the promoter is eukaryotic and the termination site is a poly A sequence containing a polyadenylation signal. Eukaryotic or mammalian promoters are known in the art and include, but are not limited to cytomegalovirus (CMV) immediate early promoter, SV40 promoter, elongation factor (EF) promoter, RSV promoter, and chicken β-actin promoter. Preferred eukaryotic polyadenylation signals are bovine growth factor (BGH) poly site, growth hormone poly A, SV40 poly A, and HSK poly A site (Foecking and Hofstetter, 1986; Kobayashi et al., 1997). Examples of eukaryotic terminators are bovine growth factor (BGH) poly A site, SV40 poly A, HSK poly A, and synthetic poly A.

Methods for transiently or stably transfecting cells with DNA/vectors are well known in the art. These include, but are not limited to calcium phosphate co-precipitation, electroporation, cationic polymer transfection, and liposome-mediated transfection (e.g. lipofection). Reagents for liposome-mediated transfection are commercially available, e.g. lipofectamine (Invitrogen) and polyethylenimine (Sigma). Cells can also be transfected by viral transfection or via viral coat particles. Another preferred method for the transfection of cells according to the present invention is the in vivo microinjection of said expression active PCR product or said expression vector and selectively growing the cells containing said expression active PCR product or said expression vector with or without the help of a selection drug. Thus, the expression active PCR product or expression vector in accordance with the present invention may additionally comprise a selectable marker.

For the generation of stable cell lines, clones can be selected using various selectable markers, which include, but are not limited to neomycin, blasticidin, puromycin, zeocin, hygromycin, and dihydrofolate reductase (dhfr).

Suitable eukaryotic/mammalian cells (host cells) for all of the above methods are also well known in the art and include, but are not limited to CHO, HEK 293, HeLa, and COS-7 cells.

In one embodiment the above method further comprises the step of translating said protein from said expression active PCR product or expression vector in said cells, preferably in said eukaryotic cells.

Preferably said protein is selected from the group comprising reporter proteins, therapeutic proteins, antibodies, vaccines, membrane proteins, fusion proteins, blood plasma proteins, cytokines, interferons, growth factors, chemokines, and GPCRs.

The objects of the present invention are also solved by a nucleic acid sequence, wherein the number of RNase L cleavage sites is reduced by at least 10%, preferably at least 25%, more preferably at least 50% (compared to the number of RNase L cleavage sites in the wild type nucleic acid sequence).

Preferably said nucleic acid sequence is produced by the method as described above.

Preferably said nucleic acid sequence is the nucleic acid sequence of a protein selected from the group comprising reporter proteins, therapeutic proteins, antibodies, vaccines, membrane proteins, fusion proteins, blood plasma proteins, cytokines, interferons, growth factors, chemokines, and GPCRs.

In one embodiment said nucleic acid sequence has a sequence selected from SEQ ID NO: 2, 3, 5, 7, 9, 11, 13, 15, 17, 19, 23, 24, 26, 28, 30-36, preferably SEQ ID NO: 9, 15, 17, 23, 30-36.

The objects of the present invention are also solved by an expression active PCR product or an expression vector comprising the nucleic acid as described above.

The objects of the present invention are further solved by a host cell containing the above expression active PCR product or expression vector.

Finally, the objects of the present invention are also solved by a protein produced by the method as described above, wherein said protein is selected from the group comprising reporter proteins, therapeutic proteins, antibodies, vaccines, membrane proteins, fusion proteins, blood plasma proteins, cytokines, interferons, growth factors, chemokines, and GPCRs.

According to the present invention the term "therapeutic proteins" is meant to include proteins used in a pharmaceutical context, such as antibody fragments, immunoglobulin chains, heavy and light chains, Fab fragments, enzymes, growth factors, interferons, cytokines, lymphokines, adhesion molecules, receptors, as well as derivatives or fragments thereof.

According to the present invention reporter proteins (either alone or fused to another protein) are particularly preferred "targets" for the above described method. There are many fluorescent and non-fluorescent reporter proteins including (without being limited to) green fluorescent proteins (GFP), red fluorescence proteins (RFP), yellow fluorescent proteins (YFP), blue and cyanine fluorescent proteins (CFP), luciferase, secreted alkaline phosphatase (SEAP), Chloramphenicol acetyltransferase (CAT), secreted hormone, secreted cytokine, β-galactosidase, and other fluorescent and bioluminescent proteins. The choice of reporter protein depends on the cell line used (endogenous activity), the nature of the experiment (e.g. dynamics of gene expression and transfection efficiency), and the adaptability of the assay to the chosen detection method (Naylor 1999). Several modifications of the reporter proteins themselves have been sought to improve the reporter performance, such as rapid response and magnitude of change, e.g. the use of destabilization elements (Li et al., 1998b; Zhao et al., 1995). Green fluorescent protein (GFP) and other fluorescent proteins are increasingly popular for the non-invasive monitoring of gene expression in living tissues, cells, and in laboratory animals (Naylor 1999). Thus, GFP (and its derivatives, such as EGFP), other fluorescent proteins (see above), as well as fusion proteins comprising a fluorescent protein are even more preferred "target proteins" for the method according to the present invention.

The inventor has surprisingly found that reducing the number of RNase L cleavage sites, preferably UU and UA dinucleotides, in the nucleic acid sequence of a protein to be expressed in a eukaryotic and/or mammalian expression system results in a significantly improved expression and yield of said protein. Without wishing to be bound to a certain theory, it is believed that the reduction of RNase L cleavage sites (i.e. reduced frequency of these sites) results in a nucleic acid sequence, namely an RNA—both primary RNA and mRNA—, that is less prone (i.e. more resistant) to attacks of endogenous RNase L in the host cells, preferably in the eukaryotic host cells, leading to increased mRNA stability and, thus increased protein expression.

Because of the universal concept involved, the present invention can be applied to any sequence. More specifically, the method according to the present invention is applicable to both endogenous and exogenous (recombinant) proteins/genes, to both stably integrated and transiently expressed genes, to proteins/genes that are difficult to express, and also to proteins/genes that are endogenously expressed in low-abundance. It can be applied to both prokaryotic and eukaryotic systems. The approach described herein will lead to a significant reduction of time and costs spent on protein production, and, thus, will allow a more efficient production of proteins/genes used as biopharmaceuticals, such as erythropoietin, growth factors, interferons, insulin, therapeutic and diagnostic antibodies, and protein- or peptide-based vaccines. It is especially useful for the expression of genes/proteins that have been proven to be very difficult to express/produce in large quantities. Examples include, but are not limited to membrane proteins, such as G-protein linked receptors (GPCR), large proteins, antibodies, fusion proteins, protein complexes, vaccines, and blood plasma proteins.

It can also help to significantly improve the expression and performance of reporter proteins, e.g. fluorescent proteins, such as GFP or luciferase, and, thus, increase the sensitivity of methods using such reporter proteins (fluorescence or luminescence microscopy, fluorescence-based microarrays, cell-sorting, etc.).

Furthermore, the approach is particularly practical and simple, since it is applicable to any cell line, such as cell lines used in the biotechnology industry including (but not limited to) hamster CHO1 and HEK293.

The following describes general principles for the step of reducing the number of RNase L cleavage sites according to the present invention:

Reduction of the Number of UU and/or UA Dinucleotides in a Coding Region

Table 2 and Table 3 show the changes that can be made. It is important to note that these modifications are entirely different from the codon usage frequency tables (see for comparison Table 1) that are used to optimize codons for protein expression on the basis of their codon bias (codon usage frequency) in a given organism. The present method is not directed at changing codons on the basis of the codon usage frequency, but in order to reduce the number of RNase L cleavage sites/targets (UU and UA dinucleotides). Moreover, the method according to the present invention is not "organism-dependent"; the number/frequency of UU and/or UA dinucleotides can be reduced in any gene (nucleic acid sequence) from any organism, as long as the corresponding amino acid sequence remains unaltered (see Tables 2 and 3). Furthermore, the reduction of the number of UU and/or UA dinucleotides can also be combined with the classical codon usage optimization for the desired organism (see for example Table 1), possibly resulting in an even more increased expression.

Table 2 shows the codons that harbor UU and/or UA dinucleotides as well as their non-UU/UA-harboring alternative(s). UUU coding for phenylalanine (Phe) can only be changed to UUC, since there is not other codon for phenylalanine that is totally devoid of UU or UA. This is also the case for tyrosine (UAU) that can only be changed to UAC.

Once the changes according to Table 2 are performed, di-triplets that form a UU or UA, i.e. NNU UNN or NNU ANN (with N being any nucleotide) are changed according to Table 3. If there is more than one alternative, preference is given to the more frequently used codon in the respective organism or in highly expressed genes.

Steps for UU and/or UA dinucleotide reduction in coding regions:
 1. Change codons according to Table 2.
 2. If more than one alternative codon exist, use the more frequently used codon in the desired organism (optional).
 3. Change the first codon of the di-triplets that form a UU or UA dinucleotide together (NNU UNN, NNU ANN) according to Table 3.
 4. If more than one alternative codon exist, use the more frequently used codon or the strongest for expression in the desired organism (optional, see Tables 4 and 5).
 5. Classical codon usage optimization (based on the host cell organism or on a list of codons most frequently used in high expression genes, can be performed optionally and preferably prior to the UU and UA reduction.

Reduction of the Number of UU and/or UA Dinucleotides in an Intron

Steps for UU and/or UA dinucleotide reduction in introns:
1. Mutate or delete one or two of the two nucleotides in UU/UA dinucleotides: UU or UA to UC, UG, GA, CA, or TA. Alternatively, insert one nucleotide.
2. The entire GC content of the intron should not be more than 80% and the length should not be changed to less than 80% of its original length.
3. Do not change exon-intron boundaries including exon donor and acceptor splice sites and branch points. Avoid disrupting the CT-rich area ranging from the splice acceptor site to the end of the branch point.

Reduction of the Number of UU and/or UA Dinucleotides in a 5'UTR

Steps for UU and/or UA dinucleotide reduction in 5'UTRs:
1. Mutate UU or UA to UC, UG, GA, CA, or TA.
2. The entire GC content of the 5'UTR should not be more than 80%.
3. Avoid context sequences near the initiation codon, ATG, since they may harbor translation enhancing sequences, such as kozac.

Reduction of the Number of UU and/or UA Dinucleotides in a 3'UTR

Steps for UU and/UA dinucleotides reduction in 3' UTRs:
1. Mutate or delete one or two of the two nucleotides in UU/UA dinucleotides: UU or UA to UC, UG, GA, CA, or TA. Alternatively, insert one nucleotide.
2. The entire GC content of the 3'UTR should not be more than 80% and the length should not be changed to less than 80% of its original length.
3. Do not change polyA signals such as AAUAAA or AUUAAA and avoid to alter any necessary or accessory sequence elements used for polyadenylation, if found.

Possible Changes in Non-Coding Regions
1. Mutation: NUUN or NUAN to NUSN (where S is G or C, and N is any nucleotide)
2. Insertion: NUUN or NUAN to NUSUN or NUSA (where S is G or C, and N is any nucleotide)
3. Deletion: NUUN to NUS (where S is G or C, and N is any nucleotide)
4. Deletion: NUAN to NAN or NUS (where S is G or C, and N is any nucleotide)

Tables

TABLE 1

Codon frequency in human genes
fields: [triplet] [amino acid] [fraction] [frequency: per thousand] ([number])

```
UUU F 0.46 17.6 (714298)   UCU S 0.19 15.2 (618711)   UAU Y 0.44 12.2 (495699)   UGU C 0.46 10.6 (430311)
UUC F 0.54 20.3 (824692)   UCC S 0.22 17.7 (718892)   UAC Y 0.56 15.3 (622407)   UGC C 0.54 12.6 (513028)
UUA L 0.08  7.7 (311881)   UCA S 0.15 12.2 (496448)   UAA * 0.30  1.0  (40285)   UGA * 0.47  1.6  (63237)
UUG L 0.13 12.9 (525688)   UCG S 0.05  4.4 (179419)   UAG * 0.24  0.8  (32109)   UGG W 1.00 13.2 (535595)

CUU L 0.13 13.2 (536515)   CCU P 0.29 17.5 (713233)   CAU H 0.42 10.9 (441711)   CGU R 0.08  4.5 (184609)
CUC L 0.20 19.6 (796638)   CCC P 0.32 19.8 (804620)   CAC H 0.58 15.1 (613713)   CGC R 0.18 10.4 (423516)
CUA L 0.07  7.2 (290751)   CCA P 0.28 16.9 (688038)   CAA Q 0.27 12.3 (501911)   CGA R 0.11  6.2 (250760)
CUG L 0.40 39.6 (1611801)  CCG P 0.11  6.9 (281570)   CAG Q 0.73 34.2 (1391973)  CGG R 0.20 11.4 (464485)

AUU I 0.36 16.0 (650473)   ACU T 0.25 13.1 (533609)   AAU N 0.47 17.0 (689701)   AGU S 0.15 12.1 (493429)
AUC I 0.47 20.8 (846466)   ACC T 0.36 18.9 (768147)   AAC N 0.53 19.1 (776603)   AGC S 0.24 19.5 (791383)
AUA I 0.17  7.5 (304565)   ACA T 0.28 15.1 (614523)   AAA K 0.43 24.4 (993621)   AGA R 0.21 12.2 (494682)
AUG M 1.00 22.0 (896005)   ACG T 0.11  6.1 (246105)   AAG K 0.57 31.9 (1295568)  AGG R 0.21 12.0 (486463)

GUU V 0.18 11.0 (448607)   GCU A 0.27 18.4 (750096)   GAU D 0.46 21.8 (885429)   GGU G 0.16 10.8 (437126)
GUC V 0.24 14.5 (588138)   GCC A 0.40 27.7 (1127679)  GAC D 0.54 25.1 (1020595)  GGC G 0.34 22.2 (903565)
GUA V 0.12  7.1 (287712)   GCA A 0.23 15.8 (643471)   GAA E 0.42 29.0 (1177632)  GGA G 0.25 16.5 (669873)
GUG V 0.46 28.1 (1143534)  GCG A 0.11  7.4 (299495)   GAG E 0.58 39.6 (1609975)  GGG G 0.25 16.5 (669768)
```

Source: http://www.kazusa.or.jp

TABLE 2

UU/UA-harboring codons and their non-UU/UA-harboring alternative(s)

| UU/UA-harboring codon | Amino acid | Alternative codon(s) |
|---|---|---|
| UUU | Phenylalanine (F) | UUC |
| UUA | Leucine (L) | CUC, CUG |
| UUG | Leucine (L) | CUC, CUG |
| CUU | Leucine (L) | CUC, CUG |
| CUA | Leucine (L) | CUC, CUG |
| UAU | Tyrosine (Y) | UAC |
| AUU | Isoleucine (I) | AUC |
| AUA | Isoleucine (I) | AUC |
| GUU | Valine (V) | GUC, GUG |
| GUA | Valine (V) | GUC, GUG |

TABLE 3

Di-Triplets forming UU/UA dinucleotides and the corresponding UU/UA-reduced di-triplet(s)

| UU/UA-forming ditriplets | Amino acid | Modified di-triplets |
|---|---|---|
| UCU UNN | Serine (S) UNN | AGC UNN |
| UCU ANN | Serine (S) ANN | AGC ANN |
| CCU UNN | Proline (P) UNN | CCC UNN or CCA UNN |
| CCU ANN | Proline (P) ANN | CCC ANN or CCA ANN |

TABLE 3-continued

Di-Triplets forming UU/UA dinucleotides and the corresponding UU/UA-reduced di-triplet(s)

| UU/UA-forming ditriplets | Amino acid | Modified di-triplets |
|---|---|---|
| ACU UNN | Threonine (T) UNN | ACC UNN or ACA UNN or ACG UNN |
| ACU ANN | Threonine (T) ANN | ACC ANN or ACA ANN or ACG ANN |
| GCU UNN | Alanine (A) UNN | GCC UNN or GCA UNN or GCG UNN |
| GCU ANN | Alanine (A) ANN | GCC ANN or GCA ANN or GCG ANN |
| CAU UNN | Histidine (H) UNN | CAC UNN |
| CAU ANN | Histidine (H) ANN | CAC ANN |
| AAU UNN | Asparagine (N) UNN | AAC UNN |
| AAU ANN | Asparagine (N) ANN | AAC ANN |
| GAU UNN | Aspartic acid (D) UNN | GAC UNN |
| GAU ANN | Aspartic acid (D) ANN | GAC ANN |
| UGU UNN | Cysteine (C) UNN | UGC UNN |
| UGU ANN | Cysteine (C) ANN | UGC ANN |
| CGU UNN | Arginine (R) UNN | CGC UNN or CGA UNN or AGA UNN or AGG UNN |
| CGU ANN | Arginine (R) ANN | CGC ANN or CGA ANN or AGA ANN or AGG ANN |
| AGU UNN | Serine (S) UNN | AGC UNN or UCC UNN or UCA UNN or UCG UNN |
| AGU ANN | Serine (S) ANN | AGC ANN or UCC ANN or UCA ANN or UCG ANN |
| GGU UNN | Glycine (G) UNN | GGA UNN or GGC UNN or GGG UNN |
| GGU ANN | Glycine (G) UNN | GGA ANN or GGC ANN or GGG ANN |

UNN: UUC, UCU, UCC, UCA, UCG,
ANN: AUC, AUG, ACU, ACC, ACA, ACG, AAU, AAC, AAA, AAG, AGU, AGC, AGA, AGG

TABLE 4

Combination of UU/UA dinucleotide reduction and classical codon optimization (for single codons/triplets)

| UU/UA codon | Amino Acid | Changed Codons | Codon bias* |
|---|---|---|---|
| UUU | Phenylalanine (F) | UUC | none |
| UUA | Leucine (L) | CUC, CUG | CUG |
| UUG | Leucine (L) | CUC, CUG | CUG |
| CUU | Leucine (L) | CUC, CUG | CUG |
| CUA | Leucine (L) | CUC, CUG | CUG |
| UAU | Tyrosine (Y) | UAC | None |
| AUU | Isoleucine (I) | AUC | None |
| AUA | Isoleucine (I) | AUC | None |
| GUU | Valine (V) | CUC, GUG | GUG |
| GUA | Valine (V) | CUC, GUG | GUG |

*Human codon bias as an example of organism codon bias.

TABLE 5

Combination of UU/UA dinucleotide reduction and classical codon optimization (for codon pairs/di-triplets)

| WU Di-Triplets | Amino Acid | Modified Di-Triplets | Codon Bias* |
|---|---|---|---|
| UCU UNN | Serine (S) UNN | AGC UNN or TCG UNN or TCC UNN | AGC UNN |
| UCU ANN | Serine (S) ANN | AGC ANN or TCG UNN or TCC ANN | AGC UNN |
| CCU UNN | Proline (P) UNN | CCC UNN or CCA UNN | CCC UNN |
| CCU ANN | Proline (P) ANN | CCC ANN or CCA ANN | CCC ANN |
| ACU UNN | Threonine (T) UNN | ACC UNN or ACA UNN or ACG UNN | ACC UNN |
| ACU ANN | Threonine (T) ANN | ACC ANN or ACA ANN or ACG ANN | ACC ANN |
| GCU UNN | Alanine (A) UNN | GCC UNN or GCA UNN GCG UNN | GCC UNN |
| GCU ANN | Alanine (A) ANN | GCC ANN or GCA ANN GCG ANN | GCC ANN |
| CAU UNN | Histidine (H) UNN | CAC UNN | None |

TABLE 5-continued

Combination of UU/UA dinucleotide reduction and classical codon optimization
(for codon pairs/di-triplets)

| WU Di-Triplets | Amino Acid | Modified Di-Triplets | Codon Bias* |
|---|---|---|---|
| CAU ANN | Histidine (H) ANN | CAC ANN | None |
| AAU UNN | Asparagine (N) UNN | AAC UNN | none |
| AAU ANN | Asparagine (N) ANN | AAC ANN | none |
| GAU UNN | Aspartic acid (D) UNN | GAC UNN | none |
| GAU ANN | Aspartic acid (D) ANN | GAC ANN | none |
| UGU UNN | Cysteine (C) UNN | UGC UNN | none |
| UGU ANN | Cysteine (C) ANN | UGC ANN | none |
| CGU UNN | Arginine (R) UNN | CGC UNN or CGA UNN or AGA UNN or AGG UNN | AGG UNN |
| CGU ANN | Arginine (R) ANN | CGC ANN or CGA ANN or AGA ANN or AGG ANN | AGG ANN |
| AGU UNN | Serine (S) UNN | AGC UNN or UCC UNN or UCA UNN or UCG UNN | AGC UNN |
| AGU ANN | Serine (S) ANN | AGC ANN or UCC ANN or UCA ANN or UCG ANN | AGC ANN |
| GGU UNN | Glycine (G) UNN | GGA UNN or GGC UNN or GGG UNN | GGC UNN |
| GGU ANN | Glycine (G) UNN | GGA ANN or GGC ANN or GGG ANN | GGC ANN |

*Human codon bias as an example of organism codon bias.
UNN: UUC, UCU, UCC, UCA, UCG,
ANN: AUC, AUG, ACU, ACC, ACA, ACG, AAU, AAC, AAA, AAG, AGU, AGC, AGA, AGG Reference is now made to the figures, wherein FIG. 1 is a graph showing the effect of the reduction of UU and UA dinucleotides on the expression of EGFP in a mammalian expression system in comparison to the wild type sequence, FIG. 2 is a graph showing the effect of the reduction of UU and UA dinucleotides on the expression of EGFP in a mammalian expression system in comparison to the wild type sequence with simultaneous over-expression of RNase L, and FIG. 3 is a graph showing the GFP fluorescence in mammalian cells transfected with PCR products harboring a modified UU/UA-reduced EGFP sequence or the wild type EGFP sequence.

Figure 1:
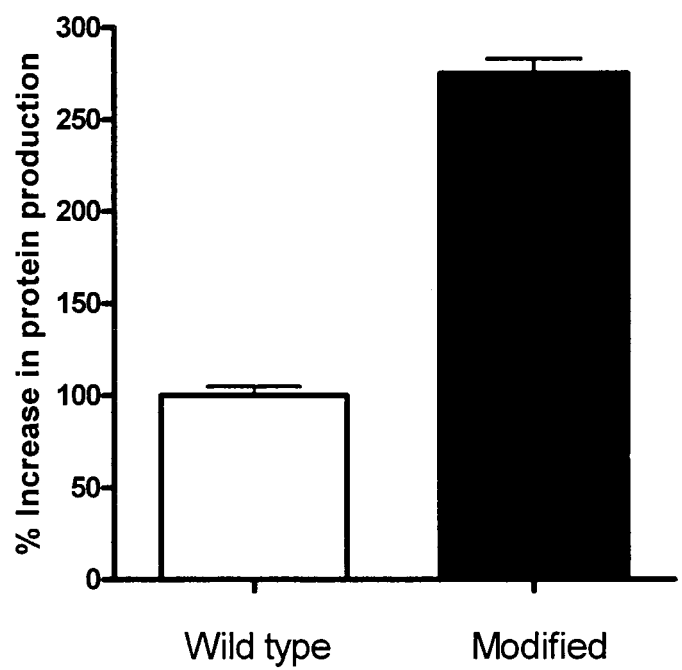

The invention is now further described by reference to the following examples, which are intended to illustrate, not to limit the scope of the invention.

EXAMPLE 1

Reduction of UU and/or UA Dinucleotides in Introns

/=splicing site

Underlined=consensus functional site

Bold underlined italics=branch point

```
SEQ ID NO: 1: Wild type rabbit beta globin
intron 1 (RBTG1):
GGTGAGGCCGA/GTTTGGTAAGTATCCTTTTTACAGCACAACTTAAT

GAGACAGATAGAAACTGACCGGTGGGAGTCTGCGGCCGCAGTCTTGT

AGAAACAGAGTAGTCGCCTGCTTTTCTGCCAGGTGCTGACTTCTCT

CCCCTTCTCTTTTTTCCTTTTCTCAG/GTTGGTGTCG

SEQ ID NO: 2: UU/UA-reduced RBTG1 (without
UU/UA reduction in the CT-rich region):
GGTGAGGCCGAGTTTGGTAAGTGTCCTCTGAACAGCACAACTGAATG

AGAAACTGACCGGTGGGAGTCTGCGGCCGCAGTCTGTAGAAACAGA

GTAGTCGCCTGCTTTTCTGCCAGGTGCTGACTTCTCTCCCCTTCTC

TTTTTTCCTTTTCTCAG/GTTGGTGTCG

SEQ ID NO: 3: UU/UA-reduced RBTG1 (with minimal
UU/UA reduction in the CT-rich region):
GGTGAGGCCGAGTTTGGTAAGTGTCCTCTGAACAGCACAACTGAATG

AGACAGAAGAAACTGACCGGTGGGAGTCTGCGGCCGCAGTCTGTAGA
```

AACAGAGTAGTCGCCTG*TCTT*CTGCCAGG**TG*C*TGAC**TCTCTCTCCC

CTTCTCTCT*C*TTCCT*C*TTCTC*AG*/GTTGGTGTCG

EXAMPLE 2

Reduction of UU and/or UA Dinucleotides in the 3'UTR

.=deletion  
Underlined=mutation  
Bold underlined=poly A signal

```
SEQ ID NO: 4: Wild type SV40 3'UTR
TGAATGCAATTGTTGTTGTTAACTTGTTTATTGCAGCTTATAATGGT

TACAAATAAAGCAATAGCATCACAAATTTCACAAATAAAGCATTTTT

TTCACTGCATTCTAGTTGTGGTTTGTCCAAAC

SEQ ID NO: 5: UU/UA-reduced SV40 3'UTR
TGAATGCAAT.GT.GC.GTCAACT.GTCTGTCTGCAGCTCACAATGG

TTACAAATAAAGCAAT.GCATCACAAATCTCACAAATCAAGCATCTG

T..CACTGCAT.CTAGT.GTGGTCTGTCCAAAC

SEQ ID NO: 6: Wild type bovine growth hormone
(BGH) 3'UTR
TCTAGAGATCTGTGTGTTGGTTTTTTGTGGATCTGCTGTGCCTTCTA

GTTGCCAGCCATCTGTTGTTTGCCCCTCCCCCGTGCCTTCCTTGACC

CTGGAAGGTGCCACTCCCACTGTCCTTTCCTAATAAAATGAGGAAAT

TGCATCGCATTGTCTGAGTAGGTGTCATTCTATTCTGGGGGGTGGGG

TGGGGCAGCACAGCAAGGGGGAGGATTGGGAAGACAATAGCAGGCAT

GCTGCTTAAG

SEQ ID NO: 7: UU/UA-reduced BGH 3'UTR
TCTAGAGATCTGTGTGTTGGTCTG.TGTGGATCTGCTGTGCCT.CTA

GT.GCCAGCCATCTGT.GTCTGCCCCTCCCCCGTGCCT.CCT.GACC

CTGGAAGGTGCCACTCCCACTGTCCTGTCCTAATAAAATGAGGAAAT

.GCATCGCAT.GTCTGAGT.GGTGTCATCTCTATCCTGGGGGTGGG

GTGGGGCAGCACAGCAAGGGGGAGGATCTGGGAAGACAAT.GCAGGC

ATGCTGCTTAAG
```

EXAMPLE 3

Reduction of UU and/or UA Dinucleotides in the Coding Region

```
SEQ ID NO: 8: Wild type enhanced green
fluorescent protein (EGFP)
ATGGCTAGCAAAGGAGAAGAACTCTTCACTGGAGTTGTCCCAATTCT

TGTTGAATTAGATGGTGATGTTAACGGCCACAAGTTCTCTGTCAGTG

GAGAGGGTGAAGGTGATGCAACATACGGAAAACTTACCCTGAAGTTC

ATCTGCACTACTGGCAAACTGCCTGTTCCATGGCCAACACTAGTCAC

TACTCTGTGCTATGGTGTTCAATGCTTTTCAAGATACCCGGATCATA

TGAAACGGCATGACTTTTTCAAGAGTGCCATGCCCGAAGGTTATGTA

CAGGAAAGGACCATCTTCTTCAAAGATGACGGCAACTACAAGACACG

TGCTGAAGTCAAGTTTGAAGGTGATACCCTTGTTAATAGAATCGAGT

TAAAAGGTATTGACTTCAAGGAAGATGGCAACATTCTGGGACACAAA

TTGGAATACAACTATAACTCACACAATGTATACATCATGGCAGACAA

ACAAAAGAATGGAATCAAAGTGAACTTCAAGACCCGCCACAACATTG

AAGATGGAAGCGTTCAACTAGCAGACCATTATCAACAAAATACTCCA

ATTGGCGATGGCCCTGTCCTTTTACCAGACAACCATTACCTGTCCAC

ACAATCTGCCCTTTCGAAAGATCCCAACGAAAAGAGAGACCACATGG

TCCTTCTTGAGTTTGTAACAGCTGCTGGGATTACACATGGCATGGAT

GAACTGTACAAC

SEQ ID NO: 9: UU/UA-reduced EGFP ("SuperGFP")
ATGGCCAGCAAGGGCGAGGAACTGTTCACCGGCGTGGTGCCCATCCT

GGTGGAGCTGGACGGCGACGTGAACGGCCACAAGTTCAGCGTGAGCG

GCGAGGGCGAAGGCGACGCCACCTACGGCAAGCTGACCCTGAAGTTC

ATCTGCACCACCGGCAAGCTGCCCGTGCCCTGGCCCACCCTGGTGAC

CACCCTGTGCTACGGCGTGCAGTGCTTCAGCAGATACCCCGACCACA

TGAAGCGGCACGACTTCTTCAAGAGCGCCATGCCCGAGGGCTACGTG

CAGGAACGGACCATCTTCTTCAAGGACGACGGCAACTACAAGACCAG

GGCCGAGGTGAAGTTCGAGGGCGACACACTGGTGAACCGGATCGAGC

TGAAGGGCATCGACTTCAAAGAGGACGGCAACATCCTGGGCCACAAG

CTGGAATACAACTACAACAGCCACAACGTGTACATCATGGCCGACAA

GCAGAAGAACGGCATCAAGGTCAACTTCAAGACCCGGCACAACATCG

AGGACGGCAGCGTGCAGCTGGCCGACCACTACCAGCAGAACACCCCC

ATCGGCGACGGCCCCGTGCTGCTGCCCGACAACCACTACCTGAGCAC

CCAGAGCGCCCTGAGCAAGGACCCCAACGAGAAGCGGGACCACATGG

TGCTGCTGGAATTCGTGACAGCCGCCGGAATCACCCACGGCATGGAC

GAGCTGTACAAC

SEQ ID NO: 10
WILD TYPE GFP SEQUENCE FROM MONTASTREA
CAVERNOSA
ATGGGCGTGATCAAGCCCGACATGAAGATCAAGCTGCGGATGGAGGG

CGCCGTGAACGGCCACAAATTCGTGATCGAGGGCGACGGGAAAGGCA

AGCCCTTTGAGGGTAAGCAGACTATGGACCTGACCGTGATCGAGGGC

GCCCCCCTGCCCTTCGCTTATGACATTCTCACCACCGTGTTCGACTA

CGGTAACCGTGTCTTCGCCAAGTACCCCAAGGACATCCCTGACTACT

TCAAGCAGACCTTCCCCGAGGGCTACTCGTGGGAGCGAAGCATGACA

TACGAGGACCAGGGAATCTGTATCGCTACAAACGACATCACCATGAT

GAAGGGTGTGGACGACTGCTTCGTGTACAAAATCCGCTTCGACGGGG

TCAACTTCCCTGCTAATGGCCCGGTGATGCAGCGCAAGACCCTAAAG

TGGGAGCCCAGTACCGAGAAGATGTACGTGCGGGACGGCGTACTGAA

GGGCGATGTTAATATGGCACTGCTCTTGGAGGGAGGCGGCCACTACC

GCTGCGACTTCAAGACCACCTACAAAGCCAAGAAGGTGGTGCAGCTT
```

-continued
CCCGACTACCACTTCGTGGACCACCGCATCGAGATCGTGAGCCACGA

CAAGGACTACAACAAAGTCAAGCTGTACGAGCACGCCGAAGCCCACA

GCGGACTACCCCGCCAGGCCGGCTAA

SEQ ID NO: 11
MONSTER-OM: MODIFIED TYPE OF SEQ ID NO: 10 BY
REDUCING THE NUMBER OF UU/UA DINUCLEOTIDES
ATGGGCGTGATCAAGCCCGACATGAAGATCAAGCTGCGGATGGAGGG

CGCCGTGAACGGCCACAAATTCGTGATCGAGGGCGACGGGAAAGGCA

AGCCCTTCGAGGGCAAGCAGACGATGGACCTGACCGTGATCGAGGGC

GCCCCCCTGCCCTTCGCCTACGACATCCTGACCACCGTGTTCGACTA

CGGCAACCGTGTCTTCGCCAAGTACCCCAAGGACATCCCTGACTACT

TCAAGCAGACCTTCCCCGAGGGCTACTCGTGGGAGCGAAGCATGACA

TACGAGGACCAGGGAATCTGCATCGCGACAAACGACATCACCATGAT

GAAGGGTGTGGACGACTGCTTCGTGTACAAAATCCGCTTCGACGGGG

TCAACTTCCCTGCCAATGGCCCGGTGATGCAGCGCAAGACCCTGAAG

TGGGAGCCCAGCACCGAGAAGATGTACGTGCGGGACGGCGTCCTGAA

GGGCGATGTGAACATGGCACTGCTCCTGGAGGGAGGCGGCCACTACC

GCTGCGACTTCAAGACCACCTACAAAGCCAAGAAGGTGGTGCAGCTG

CCCGACTACCACTTCGTGGACCACCGCATCGAGATCGTGAGCCACGA

CAAGGACTACAACAAAGTCAAGCTGTACGAGCACGCCGAAGCCCACA

GCGGACTGCCCCGCCAGGCCGGCTGAAGTCTCACGGCTTCCCACCCG

AGGTCGAGGAGCAGGATGATGGCACACTGCCCATGAGCTGTGCTCAG

GAGTCTGGCATGGACAGACACCCCGCTGCCTGTGCCAGTGCCAGGAT

CAATGTG TGA

SEQ ID NO: 12
CLAVULARIA SPECIES-WILD TYPE SEQUENCE
ATGGTGAGCAAGGGCGAGGAGACCACAATGGGCGTAATCAAGCCCGA

CATGAAGATCAAGCTGAAGATGGAGGGCAACGTGAATGGCCACGCCT

TCGTGATCGAGGGC GAGGGCGAGGGCAAGCCCTACGACGGCACCAA

CACATCAACCTGGAGGTGAAGGAGGGAGCCCCCCTGCCCTTCTCCTA

CGACATTCTGACCACCGCGTTCAGTTACGGCAACAGGGCCTTCACCA

AGTACCCCGACGACATCCCCAACTACTTCAAGCAGTCCTTCCCCGAG

GGCTACTCTTGGGAGCGCACCATGACCTTCGAGGACAAGGGCATCGT

GAAGGTGAAGTCCGACATCTCCATGGAGGAGGACTCCTTCATCTACG

AGATACACCTCAAGGGCGAGAACTTCCCCCCCAACGGCCCCGTGATG

CAGAAGGAGACCACCGGCTGGGACGCCTCCACCGAGAGGATGTACGT

GCGCGACGGCGTGCTGAAGGGCGACGTCAAGATGAAGCTGCTGCTGG

AGGGCGGCGGCCACCACCGCGTTGACTTCAAGACCATCTACAGGGCC

AAGAAGGCGGTGAAGCTGCCCGACTATCACTTTGTGGACCACCGCAT

CGAGATCCTGAACCACGACAAGGACTACAACAAGGTGACCGTTTACG

AGATCGCCGTGGCCCGCAACTCCACCGACGGCATGGACGAGCTGTAC

AAGTAA

SEQ ID NO.: 13
CLAVULARIA SPECIES-OM: MODIFIED
(UU/UA-reduced)
ATGGTGAGCAAGGGCGAGGAGACCACAATGGGCGTGATCAAGCCCGA

CATGAAGATCAAGCTGAAGATGGAGGGCAACGTGAATGGCCACGCCT

TCGTGATCGAGGGCGAGGGCGAGGGCAAGCCCTACGACGGCACCAAC

ACCATCAACCTGGAGGTGAAGGAGGGAGCCCCCCTGCCCTTCTCCTA

CGACATCCTGACCACCGCGTTCAGCTACGGCAACAGGGCCTTCACCA

AGTACCCCGACGACATCCCCAACTACTTCAAGCAGTCCTTCCCCGAG

GGCTACAGCTGGGAGCGCACCATGACCTTCGAGGACAAGGGCATCGT

GAAGGTGAAGTCCGACATCTCCATGGAGGAGGACTCCTTCATCTACG

AGATCCACCTCAAGGGCGAGAACTTCCCCCCCAACGGCCCCGTGATG

CAGAAGGAGACCACCGGCTGGGACGCCTCCACCGAGAGGATGTACGT

GCGCGACGGCGTGCTGAAGGGCGAGCGTCAAGATGAAGCTGCTGCTG

GAGGGCGGCGGCCACCACCGCGTGGACTTCAAGACCATCTACAGGGC

CAAGAAGGCGGTGAAGCTGCCCGACTATCACTTCGTGGACCACCGCA

TCGAGATCCTGAACCACGACAAGGACTACAACAAGGTACCGTGTACG

AGATCGCCGTGGCCCGCAACTCCACCGACGGCATGGACGAGCTGTAC

AAGCTGA

SEQ ID NO: 14
FIREFLY LUCIFERASE +: WILD TYPE SEQUENCE:
ATGGAAGACGCCAAAAACATAAAGAAAGGCCCGGCGCCATTCTATCC

GCTGGAAGATGGAACCGCTGGAGAGCAACTGCATAAGGCTATGAAGA

GATACGCCCTGGTTCCTGGAACAATTGCTTTTACAGATGCACATATC

GAGGTGGACATCACTTACGCTGAGTACTTCGAAATGTCCGTTCGGTT

GGCAGAAGCTATGAAACGATATGGGCTGAATACAAATCACAGAATCG

TCGTATGCAGTGAAAACTCTCTTCAATTCTTTATGCCGGTGTTGGGC

GCGTTATTTTATCGGAGTTGCAGTTGCGCCCGCGAACGACATTTATA

ATGAACGTGAATTGCTCAACAGTATGGGCATTTCGCAGCCTACCGTG

GTGTTCGTTTCCAAAAAGGGGTTGCAAAAAATTTTGAACGTGCAAAA

AAAGCTCCCAATCATCCAAAAAATTATTATCATGGATTCTAAAACGG

ATTACCAGGGATTTCAGTCGATGTACACGTTCGTCACATCTCATCTA

CCTCCCGGTTTTAATGAATACGATTTTGTGCCAGAGTCCTTCGATAG

GGACAAGACAATTGCACTGATCATGAACTCCTCTGGATCTACTGGTC

TGCCTAAAGGTGTCGCTCTGCCTCATAGAACTGCCTGCGTGAGATTC

TCGCATGCCAGAGATCCTATTTTTGGCAATCAAATCATTCCGGATAC

TGCGATTTTAAGTGTTGTTCCATTCCATCACGGTTTTGGAATGTTTA

CTACACTCGGATATTTGATATGTGGATTTCGAGTCGTCTTAATGTAT

AGATTTGAAGAAGAGCTGTTTCTGAGGAGCCTTCAGGATTACAAGAT

TCAAAGTGCGCTGCTGGTGCCAACCCTATTCTCCTTCTTCGCCAAAA

GCACTCTGATTGACAAATACGATTTATCTAATTTACACGAAATTGCT

TCTGGTGGCGCTCCCCTCTCTAAGGAAGTCGGGGAAGCGGTTGCCAA

GAGGTTCCATCTGCCAGGTATCAGGCAAGGATATGGGCTCACTGAGA

CTACATCAGCTATTCTGATTACACCCGAGGGGATGATAAACCGGGC

GCGGTCGGTAAAGTTGTTCCATTTTTTGAAGCGAAGGTTGTGGATCT

GGATACCGGGAAAACGCTGGGCGTTAATCAAAGAGGCGAACTGTGTG

TGAGAGGTCCTATGATTATGTCCGGTTATGTAAACAATCCGGAAGCG

ACCAACGCCTTGATTGACAAGGATGGATGGCTACATTCTGGAGACAT

AGCTTACTGGGACGAAGACGAACACTTCTTCATCGTTGACCGCCTGA

AGTCTCTGATTAAGTACAAAGGCTATCAGGTGGCTCCCGCTGAATTG

GAATCC

SEQ ID NO: 15
LUC + DU (Superluciferase): (UU/UA-reduced)
ATGGAAGACGCCAAAAACATCAAGAAAGGCCCGGCGCCATTCTACCC

GCTGGAAGATGGAACCGCTGGAGAGCAACTGCACAAGGCCATGAAGA

GATACGCCCTGGTGCCTGGAACAATCGCGTTCACAGATGCACACATC

GAGGTGGACATCACCTACGCTGAGTACTTCGAAATGTCCGTCCGGCT

GGCAGAAGCCATGAAACGATACGGGCTGAACACAAATCACAGATCGT

CGTGTGCAGTGAAAACTCTCTGCAATTCTTCATGCCGGTGCTGGGCG

CGCTGTTCATCGGAGTGGCAGTCGCGCCCGCGAACGACATCTACAAT

GAACGTGAACTCCTCAACAGCATGGGCATCTCGCAGCCCACCGTGGT

GTTCGTGTCCAAAAAGGGGCTGCAAAAAATCCTGAACGTGCAAAAAA

AGCTCCCAATCATCCAAAAAATCATCATCATGGACAGCAAAACGGAC

TACCAGGGATTCCAGTCGATGTACACGTTCGTCACATCTCATCTGCC

TCCCGGCTTCAATGAATACGACTTCGTGCCAGAGTCCTTCGACAGGG

ACAAGACAATCGCACTGATCATGAACTCCTCTGGAAGCACTGGTCTG

CCCAAAGGTGTCGCTCTGCCTCACAGAACTGCCTGCGTGAGATTCTC

GCATGCCAGAGATCCCATCTTCGGCAATCAAATCATCCCGGACACTG

CGATCCTGAGTGTGGTCCCATTCCATCACGGCTTCGGAATGTTCACG

ACACTCGGATACCTGATCTGTGGATTCCGAGTCGTCCTGATGTACAG

ATTCGAAGAAGAGCTGTTCCTGAGGAGCCTCCAGGACTACAAGATCC

AAAGTGCGCTGCTGGTGCCAACCCTGTTCTCCTTCTTCGCCAAAAGC

ACTCTGATCGACAAATACGATCTCAGCAATCTGCACGAAATCGCCTC

TGGTGGCGCTCCCCTCTCCAAGGAAGTCGGGGAAGCGGTCGCCAAGA

GGTTCCATCTGCCAGGGATCAGGCAAGGATACGGGCTCACTGAGACG

ACATCAGCCATCCTGATCACACCCGAGGGGGATGACAAACCGGGCGC

GGTCGGGAAAGTGGTCCATTCTTCGAAGCGAAGGTTGTGGATCTGG

ACACCGGGAAAACGCTGGGCGTTAATCAAAGAGGCGAACTGTGTGTG

AGAGGTCCATGATCATGTCCGGCTACGTGAACAATCCGGAAGCGAC

CAACGCCCTGATCGACAAGGATGGATGGCTCCACTCTGGAGACATCG

CGTACTGGGACGAAGACGAACACTTCTTCATCGTGGACCGCCTGAAG

TCTCTGATCAAGTACAAAGGCTACCAGGTGGCTCCCGCTGAACTCGA

ATCCATCCTGCTCCAACACCCCAACATCTTCGACGCAGGTGTCGCAG

GTCTGCCCGACGATGACGCCGGTGAACTGCCCGCCGCCGTCGTGGTT

CTGGAGCACGGAAAGACGATGACGGAAAAAGAGATCGTGGACTACGT

CGCCAGTCAAGTAACAACCGCGAAAAAGCTGCGCGGAGGAGTTGTGT

TCGTGGACGAAGTGCCGAAAGGTCTGACCGGAAAACTCGACGCAAGA

AAAATCAGAGAGATCCTCATCAAGGCCAAGAAGGGCGGAAAGATCGC

CGTG

SEQ ID NO: 16
Firefly LUC2 luciferase wildtype:
ATGGAAGATGCCAAAAACATTAAGAAGGGCCCAGCGCCATTCTACCC

ACTCGAAGACGGGACCGCCGGCGAGCAGCTGCACAAAGCCATGAAGC

GCTACGCCCTGGTGCCCGGCACCATCGCCTTTACCGACGCACATATC

GAGGTGGACATTACCTACGCCGAGTACTTCGAGATGAGCGTTCGGCT

GGCAGAAGCTATGAAGCGCTATGGGCTGAATACAAACCATCGGATCG

TGGTGTGCAGCGAGAATAGCTTGCAGTTCTTCATGCCCGTGTTGGGT

GCCCTGTTCATCGGTGTGGCTGTGGCCCCAGCTAACGACATCTACAA

CGAGCGCGAGCTGCTGAACAGCATGGGCATCAGCCAGCCCACCGTCG

TATTCGTGAGCAAGAAAGGGCTGCAAAAGATCCTCAACGTGCAAAAG

AAGCTACCGATCATACAAAAGATCATCATCATGGATAGCAAGACCGA

CTACCAGGGCTTCCAAAGCATGTACACCTTCGTGACTTCCCATTTGC

CACCCGGCTTCAACGAGTACGACTTCGTGCCCGAGAGCTTCGACCGG

GACAAAACCATCGCCCTGATCATGAACAGTAGTGGCAGTACCGGATT

GCCCAAGGGCGTAGCCCTACCGCACCGCACCGCTTGTGTCCGATTCA

GTCATGCCCGCGACCCCATCTTTCGGCAACCAGATCATCCCCGACAC

CGCTATCCTCAGCGTGGTGCCATTTCACCACGGCTTCGGCATGTTCA

CCACGCTGGGCTACTTGATCTGCGGCTTTCGGGTCGTGCTCATGTAC

CGCTTCGAGGAGGAGCTATTCTTGCGCAGCTTGCAAGACCTATAAGA

TTCAATCTGCCCTGCTGGTGCCCACACTATTTAGCTTCTTCGCTAAG

AGCACTCTCATCGACAAGTACGACCTAAGCAACTTGCACGAGATCGC

CAGCGGCGGGGCGCCGCTCAGCAAGGAGGTAGGTGAGGCCGTGGCCA

AACGCTTCCACCTACCAGGCATCCGCCAGGGCTACGGCCTGACAGAA

ACAACCAGCGCCATTCTGATCACCCCCGAAGGGGACGACAAGCCTGG

CGCAGTAGGCAAGGTGGTGCCCTTCTTCGAGGCTAAGGTGGTGGACT

TGGACACCGGTAAGACACTGGGTGTGAACCAGCGCGGCGAGCTGTGC

GTCCGTGGCCCCATGATCATGAGCGGCTACGTTAACAACCCCGAGGC

TACAAACGCTCTCATCGACAAGGACGGCTGGCTGCACAGCGGCGACA

TCGCCTACTGGGACGAGGACGAGCACTTCTTCATCGTGGACCGGCTG

AAGAGCCTGATCAAATACAAGGGCTACCAGGTAGCCCCAGCCGAACT

GGAGAGCATCCTGCTGCAACACCCCAACATCTTCGACGCCGGGGTCG

CCGGCCTGCCCGACGACGATGCCGGCGAGCTGCCCGCCGCAGTCGTC

GTGCTGGAACACGGTAAAACCATGACCGAGAAGGAGATCGTGGACTA

TGTGGCCAGCCAGGTTACAACCGCCAAGAAGCTGCGCGGTGGTGTTG

TGTTCGTGGACGAGGTGCCTAAAGGACTGACCGGCAAGTTGGACGCC

CGCAAGATCCGCGAGATTCTCATTAAGGCCAAGAAGGGCGGCAAGAT

CGCCGTGTAATAA

SEQ ID NO: 17
LUC2OM: LUC2 modified SuperLuciferase2
(UU/UA-reduced)
ATGGAAGATGCCAAAAACATCAAGAAGGGCCCAGCGCCATTCTACCC

ACTCGAAGACGGGACCGCAGGCGAGCAGCTGCACAAAGCCATGAAGC

GCTACGCCCTGGTGCCCGGCACCATCGCCTTCACCGACGCACACATC

GAGGTGGACATCACCTACGCCGAGTACTTCGAGATGAGCGTGCGGCT

GGCAGAAGCCATGAAGCGCTACGGGCTGAACACAAACCATCGGATCG

TGGTGTGCAGCGAGAACAGCCTGCAGTTCTTCATGCCCGTGCTGGGT

GCCCTGTTCATCGGTGTGGCTGTGGCCCCAGCCAACGACATCTACAA

CGAGCGCGAGCTGCTGAACAGCATGGGCATCAGCCAGCCCACCGTCG

TGTTCGTGAGCAAGAAAGGGCTGCAAAAGATCCTCAACGTGCAAAAG

AAGCTGCCGATCATCCAAAAGATCATCATCATGGACAGCAAGACCGA

CTACCAGGGCTTCCAAAGCATGTACACCTTCGTGACCTCCCACCTGC

CACCCGGCTTCAACGAGTACGACTTCGTGCCCGAGAGCTTCGACCGG

GACAAAACCATCGCCCTGATCATGAACAGCAGTGGCAGCACCGGACT

GCCCAAGGGCGTGGCACTGCCGCACCGCACCGCCTGTGTCCGATTCA

GTCATGCACGCGACCCCATCTTCGGCAACCAGATCATCCCCGACACC

GCCATCCTCAGCGTGGTGCCATTCCACCACGGCTTCGGCATGTTCAC

CACGCTGGGCTACTGGATCTGCGGCTTCCGGGTCGTGCTCATGTACC

GCTTCGAGGAGGAGCTGTTCCTGCGCAGCCTGCAAGACTACAAGATC

CAATCTGCCCTGCTGGTGCCCACACTGTTCAGCTTCTTCGCCAAGAG

CACTCTCATCGACAAGTACGACCTGAGCAACCTGCACGAGATCGCCA

GCGGCGGAGCGCCGCTCAGCAAGGAGGTGGGTGAGGCCGTGGCCAAA

CGCTTCCACCTGCCAGGCATCCGCCAGGGCTACGGCCTGACAGAAAC

AACCAGCGCCATTCTGATCACCCCCGAAGGGGACGACAAGCCTGGCG

CAGTGGGCAAGGTGGTGCCCTTCTTCGAGGCCAAGGTGGTGGACCTG

GACACCGGCAAGACACTGGGTGTGAACCAGCGCGGCGAGCTGTGCGT

CCGTGGCCCCATGATCATGAGCGGCTACGTGAACAACCCCGAGGCCA

CAAACGCTCTCATCGACAAGGACGGCTGGCTGCACAGCGGCGACATC

GCCTACTGGGACGAGGACGAGCACTTCTTCATCGTGGACCGGCTGA

AGAGCCTGATCAAATACAAGGGCTACCAGGTGGCCCCAGCCGAACTG

GAGAGCATCCTGCTGCAACACCCCAACATCTTCGACGCCGGAGTCGC

CGGACTGCCAGACGACGATGCCGGCGAGCTGCCCGCAGCAGTCGTCG

TGCTGGAACACGGCAAAACCATGACCGAGAAGGAGATCGTGGACTAC

GTGGCCAGCCAGGTGACAACCGCCAAGAAGCTGCGCGGTGGTGTGGT

GTTCGTGGACGAGGTGCCCAAAGGACTGACCGGCAAGCTGGACGCCC

GCAAGATCCGCGAGATCCTCATCAAGGCCAAGAAGGGCGGCAAGATC

GCCGTGTGA

SEQ ID NO: 18
Puntellina Plumate (GFP) wild type:
ATGGAGAGCGACGAGAGCGGCCTGCCCGCCATGGAGATCGAGTGCCG

CATCACCGGCACCCTGAACGGCGTGGAGTTCGAGCTGGTGGGCGGCG

GAGAGGGCACCCCCGAGCAGGGCCGCATGACCAACAAGATGAAGAGC

ACCAAAGGCGCCCTGACCTTCAGCCCCTACCTGCTGAGCCACGTGAT

GGGCTACGGCTTCTACCACTTCGGCACCTACCCCAGCGGCTACGAGA

ACCCCTTCCTGCACGCCATCAACAACGGCGGCTACACCAACACCCGC

ATCGAGAAGTACGAGGACGGCGGCGTGCTGCACGTGAGCTTCAGCTA

CCGCTACGAGGCCGGCCGCGTGATCGGCGACTTCAAGGTGATGGGCA

CCGGCTTCCCCGAGGACAGCGTGATCTTCACCGACAAGATCATCCGC

AGCAACGCCACCGTGGAGCACCTGCACCCCATGGGCGATAACGATCT

GGATGGCAGCTTCACCCGCACCTTCAGCCTGCGCGACGGCGGCTACT

ACAGCTCCGTGGTGGACAGCCACATGCACTTCAAGAGCGCCATCCAC

CCCAGCATCCTGCAGAACGGGGGCCCCATGTTCGCCTTCCGCCGCGT

GGAGGAGGATCACAGCAACACCGAGCTGGGCATCGTGGAGTACCAGC

ACGCCTTCAAGACCCCGGATGCAGATGCCGGTGAAGAAA

SEQ ID NO: 19
Puntellina Plumate (GFP): modified sequence
(UU/UA-reduced)
ATGGAGAGCGACGAGAGCGGCCTGCCCGCCATGGAGATCGAGTGCCG

CATCACCGGCACCCTGAACGGCGTGGAGTTCGAGCTGGTGGGCGGCG

GAGAGGGCACCCCCGAGCAGGGCCGCATGACCAACAAGATGAAGAGC

ACCAAAGGCGCCCTGACCTTCAGCCCCTACCTGCTGAGCCACGTGAT

GGGCTACGGCTTCTACCACTTCGGCACCTACCCCAGCGGCTACGAGA

ACCCCTTCCTGCACGCCATCAACAACGGCGGCTACACCAACACCCGC

ATCGAGAAGTACGAGGACGGCGGCGTGCTGCACGTGAGCTTCATCTA

CCGCTACGAGGCCGGCCGCGTGATCGGCGACTTCAAGGTGATGGGCA

CCGGCTTCCCCGAGGACAGCGTGATCTTCACCGACAAGATCATCCGC

AGCAACGCCACCGTGGAGCACCTGCACCCCATGGGCGACAACGACCT

GGATGGCAGCTTCACCCGCACCTTCAGCCTGCGCGACGGCGGCTACT

ACAGCTCCGTGGTGGACAGCCACATGCACTTCAAGAGCGCCATCCAC

CCCAGCATCCTGCAGAACGGGGGCCCCATGTTCGCCTTCCGCCGCGT

GGAGGAGGATCACAGCAACACCGAGCTGGGCATCGTGGAGATACCAG

CACGCCTTCAAGACCCCGGATGCAGATGCCGGTGAAGAACTGA

SEQ ID NO: 20
Red Fluorescent protein from Discosoma wild
type sequence
atgagcgagctgatcaaggagaacatgcacatgaagctgtacatgga gggcaccgtgaacaaccaccacttcaagtgcacatccgagggcgaag gcaagccctacgagggcacccagaccatgaagatcaaggtggtcgag ggcggccctctccccttcgccttcgacatcctggctaccagcttcat gtacggcagcaaagccttcatcaaccacacccagggcatccccgact tctttaagcagtccttccctgagggcttcacatgggagagaatcacc -continued
acatacgaagacgggggcgtgctgaccgctacccaggacaccagctt
ccagaacggctgcatcatctacaacgtcaagatcaacggggtgaact
tcccatccaacggccctgtgatgcagaagaaaacacgcggctgggag
gccaacaccgagatgctgtaccccgctgacggcggcctgagaggcca
cagccagatggccctgaagctcgtgggcggggctacctgcactgct
ccttcaagaccacatacagatccaagaaacccgctaagaacctcaag
atgcccggcttccacttcgtggaccacagactggaaagaatcaagga
ggccgacaaagagacctacgtcgagcagcacgagatggctgtggcca
agtactgcgacctccctagcaaactggggcacagagatga SEQ ID NO: 21
Red Fluorescent protein modified sequence
ATGAGCGAGCTGATCAAGGAGAACATGCACATGAAGCTGTACATGGA
GGGCACCGTGAACAACCACCACTTCAAGTGCACATCCGAGGGCGAAG
GCAAGCCCTACGAGGGCACCCAGACCATGAAGATCAAGGTGGTCGAG
GGCGGCCCACTCCCCTTCGCCTTCGACATCCTGGCCACCAGCTTCAT
GTACGGCAGCAAAGCCTTCATCAACCACACCCAGGGCATCCCCGACT
TCTTCAAGCAGTCCTTCCCTGAGGGCTTCACATGGGAGAGAATCACC
ACATACGAAGACGGGGGCGTGCTGACCGCACCCAGGACACCAGCTTC
CAGAACGGCTGCATCATCTACAACGTCAAGATCAACGGGGTGAACTT
CCCATCCAACGGCCCTGTGATGCAGAAGAAAACACGCGGCTGGGAGG
CCAACACCGAGATGCTGTACCCCGCTGACGGCGGCCTGAGAGGCCAC
AGCCAGATGGCCCTGAAGCTCGTGGGCGGGGCTACCTGCACTGCTC
CTTCAAGACCACATACAGATCCAAGAAACCCGCCAAGAACCTCAAGA
TGCCCGGCTTCCACTTCGTGGACCACAGACTGGAAAGAATCAAGGAG
GCCGACAAAGAGACCTACGTCGAGCAGCACGAGATGGCTGTGGCCAA
GTACTGCGACCTCCCAAGCAAACTGGGGCACAGAC SEQ ID NO: 22
Hepatitis B surface antigen wild type, adr
hepatitis B virus strain:
ATGGAGAACACAACATCAGGATTCCTAGGACCCCTGCTCGTGTTACA
GGCGGGGTTTTCTTGTTGACAAGAATCCTCACAATACCACAGAGTC
TAGACTCGTGGTGGACTTCTCTCAATTTTCTAGGGGAGCACCCACG
TGTCCTGGCCCAAATTCGCAGTCCCCAACCTCCAATCACTCACCAAC
CTCTTGTCCTCCAATTTGTCCTGGCTATTCGCTGGATGTGTCTGCGG
CGTTTTATCATATTCCTCTTCATCCTGCTGCTATGCCTCATCTTCTT
GTTGGTTCTTCTGGACTACCAAGGTATGTTGCCCGTTTGTCCTCTAC
TTCCAGGAACATCAACTACCAGCACGGGACCATGCAAGACCTGCACG
ATTCCTGCTCAAGGAACCTCTATGTTTCCTCCTGTTGCTGTACAAA
ACCTTCGGACGGAAACTGCACTTGTATTCCCATCCCATCATCCTGGG
CTTTCGCAAGATTCCTATGGGAGTGGGCCTCAGTCCGTTTCTCCTGG
CTCAGTTTACTAGTGCCATTGTTCAGTGGTTCGTAGGGCTTTCCCC
CACTGTTTGGCTTTCAGTTATATGGATGATGTGGTATTGGGGGCCAA -continued
GTCTGTACAACATCTTGAGTCCCTTTTTTACCTCTATTACCAATTTTC
TTTTGTCTTTGGGTATACATTTGA SEQ ID NO: 23
HBSAGOM: Hepatitis B surface antigen modified
sequence:
ATGGAGAACACCACCAGCGGCTTCCTGGGCCCTCTGCTGGTGCTGCA
GGCCGGCTTCTTCCTGCTGACCCGCATCCTGACCATCCCCCAGAGCC
TGGACAGCTGGTGGACCAGCCTGAACTTCCTGGGCGGAGCCCCAACC
TGTCCCGGCCCAACAGCCAGAGCCCCACCAGCAACCACAGCCCAAC
CAGCTGCCCACCCATCTGTCCCGGCTACCGGTGGATGTGCCTGCGGC
GGTTCATCATCTTCCTGTTCATCCTGCTGCTGTGCCTGATCTTCCTC
CTGGTGCTCCTGGACTACCAGGGCATGCTGCCCGTGTGTCCTCTGCT
GCCTGGCACCAGCACCACCTCCACCGGCCCCTGCAAGACCTGCACAA
TCCCCGCCCAGGGAACCAGCATGTTCCCAAGCTGCTGCTGCACCAAG
CCCAGCGACGGCAACTGCACCTGCATCCCCATCCCAAGCAGCTGGGC
CTTCGCCAGATTCCTGTGGGAGTGGGCCTCCGTGAGATTCAGCTGGC
TGTCACTGCTGGTGCCCTTCGTGCAGTGGTTCGTGGGCCTGAGCCCA
ACAGTGTGGCTGAGCGTGATCTGGATGATGTGGTACTGGGGACCCAG
CCTGTACAACATCCTGAGCCCCTTCCTGCCCCTGCTGCCCATCTTCT
TCTGCCTGTGGGTGTACATCTGA SEQ ID NO: 24
HBSAGM: HBSAGOM: Hepatitis B surface antigen
modified sequence 2
ATGGAGAACACAACATCAGGATTCCTCGGACCCCTGCTCGTGCTGCA
GGCGGGGTTCTTCCTGCTCACAAGAATCCTCACAATCCCACAGAGTC
TGGACTCGTGGTGGACGTCTCTCAACTTCCTCGGGGGAGCACCCACG
TGTCCTGGCCCAAACTCGCAGTCCCCAACCTCCAATCACTCACCAAC
CTCGTGTCCTCCAATCTGTCCTGGCTACCGCTGGATGTGTCTGCGGC
GCTTCATCATCTTCCTCTTCATCCTGCTGCTGTGCCTCATCTTCCTG
CTCGTCCTCCTGGACTACCAAGGGATGCTGCCCGTCTGTCCTCTGCT
GCCAGGAACATCAACCACCAGCACGGGACCATGCAAGACCTGCACGA
TCCCTGCTCAAGGAACCAGCATGTTCCCCTCCTGCTGCTGCACAAAA
CCATCGGACGGAAACTGCACCTGCATCCCCATCCCATCATCCTGGGC
CTTCGCAAGATTCCTCTGGGAGTGGGCCTCAGTCCGGTTCTCCTGGC
TCAGTCTCCTGGTGCCATTCGTGCAGTGGTTCGTCGGGCTGTCCCCC
ACTGTGTGGCTGTCAGTGATCTGGATGATGTGGTACTGGGGGCCAAG
TCTGTACAACATCCTCAGTCCCTTCCTGCCTCTGCTGCCAATCTTCT
TCTGTCTGTGGGTGTACATCTGA This sequence includes both an UU/UA reduction
as well as a humanization.

SEQ ID NO: 25
IFN-ALPHA, HUMAN
ATGGCCTTGACCTTTGCTTTACTGGTGGCCCTCCTGGTGCTCAGCTG
CAAGTCAAGCTGCTCTGTGGGCTGTGATCTGCCTCAAACCCACAGCC
TGGGTAGCAGGAGGACCTTGATGCTCCTGGCACAGATGAGGAGAATC

-continued

TCTCTTTTCTCCTGCTTGAAGGACAGACATGACTTTGGATTTCCCCA

GGAGGAGTTTGGCAACCAGTTCCAAAAGGCTGAAACCATCCCTGTCC

TCCATGAGATGATCCAGCAGATCTTCAATCTCTTCAGCACAAAGGAC

TCATCTGCTGCTTGGGATGAGACCCTCCTAGACAAATTCTACACTGA

ACTCTACCAGCAGCTGAATGACCTGGAAGCCTGTGTGATACAGGGGG

TGGGGGTGACAGAGACTCCCCTGATGAAGGAGGACTCCATTCTGGCT

GTGAGGAAATACTTCCAAAGAATCACTCTCTATCTGAAAGAGAAGAA

ATACAGCCCTTGTGCCTGGGAGGTTGTCAGAGCAGAAATCATGAGAT

CTTTTTCTTTGTCAACAAACTTGCAAGAAAGTTTAAGAAGTAAGGAA

TGA

SEQ ID NO: 26
IFN-ALPHAOM: modified sequence
ATGGCCCTGACCTTCGCCCTGCTGGTGGCTCTGCTGGTGCTGAGCTG

CAAGAGCAGCTGCAGCGTGGGCTGCGATCTGCCTCAGACCCACAGCC

TGGGCAGCAGACGGACACTGATGCTGCTGGCCCAGATGCGGCGGATC

AGCCTGTTCAGCTGCCTGAAGGACCGGCACGACTTCGGCTTCCCCCA

GGAAGAGTTCGGCAACCAGTTCCAGAAGGCCGAGACAATCCCCGTGC

TGCACGAGATGATCCAGCAGATCTTCAACCTGTTCAGCACCAAGGAC

AGCAGCGCCGCCTGGGACGAGACACTGCTGGACAAGTTCTACACCGA

GCTGTACCAGCAGCTGAACGACCTGGAAGCCTGCGTGATCCAGGGCG

TGGGCGTGACCGAGACACCCCTGATGAAGGAAGACAGCATCCTGGCC

GTGCGGAAGTACTTCCAGCGGATCACCCTGTACCTGAAAGAGAAGAA

GTACAGCCCCTGCGCCTGGGAAGTGGTCCGGGCCGAGATCATGCGGA

GCTTCAGCCTGAGCACCAACCTGCAGGAAAGCCTGCGGAGCAAAGAG

ATGA

SEQ ID NO: 27
CSF3M Colony stimulating factor wild type
sequence, human:
ATGGCTGGACCCTGCCACCCAGAGCCCCATGAAGCTGATGGCCCTGC

AGCTGCTGCTGTGGCACAGTGCACTCTGGACAGTGCAGGAAGCCACC

CCCCTGGGCCCTGCCAGCTCCCTGCCCCAGAGCTTCCTGCTCAAGTG

CTTAGAGCAAGTGAGGAAGATCCAGGGCGATGGCGCAGCGCTCCAGG

AGAAGCTGTGTGCCACCTACAAGCTGTGCCACCCCGAGGAGCTGGTG

CTGCTCGGACACTCTCTCGGGCATCCCCTGGGCTCCCCTGAGCAGCT

GCCCCAGCCAGGCCCTGCAGCTGGCAGGCTGCTTGAGCCAACTCCAT

AGCGGCCTTTTCCTCTACCAGGGGCTCCTGCAGGCCCTGGAAGGGAT

CTCCCCCGAGTTGGGTCCCACCTTGGACACACTGCAGCTGGACGTCG

CCGACTTTGCCACCACCATCTGGCAGCAGATGGAAGAACTGGGAATG

GCCCCTGCCCTGCAGCCCACCCAGGGTGCCATGCCGGCCTTCGCCTC

TGCTTTCCAGCGCCGGGCAGGAGGGGTCCTAGTTGCCTCCCATCTGC

AGAGCTTCCTGGAGGTGTCGTACCGCGTTCTACGCCACCTTGCCCAG

CCC

SEQ ID NO: 28
CSF3M Colony stimulating factor modified
sequence,:
ATGGCTGGACCTGCCACCCAGAGCCCCATGAAGCTGATGGCCCTGCA

GCTGCTGCTGTGGCACAGTGCACTCTGGACAGTGCAGGAAGCCACCC

CCCTGGGCCCTGCCAGCTCCCTGCCCCAGAGCTTCCTGCTCAAGTGC

CTGGAGCAAGTGAGGAAGATCCAGGGCGATGGCGCCAGCGCTCCAGG

AGAAGCTGTGTGCCACCTACAAGCTGTGCCACCCCGAGGAGCTGGTG

CTGCTCGGACACTCTCTGGGCATCCCCTGGGCTCCCCTGAGCAGCTG

CCCCAGCCAGGCCCTGCAGCTGGCAGGCTGCCTGAGCCAACTCCACA

GCGGCCTCTTCCTCTACCAGGGGCTCCTGCAGGCCCTGGAAGGGATC

TCCCCCGAGCTGGGTCCCACCCTGGACACACTGCAGCTGGACGTCGC

CGACTTCGCCACCACCATCTGGCAGCAGATGGAAGAACTGGGAATGG

CCCCTGCCCTGCAGCCCACCCAGGGTGCCATGCCGGCCTTCGCCTCT

GCCTTCCAGCGCCGGGCAGGAGGGGTCCTGGTGGCCTCCCATCTGCA

GAGCTTCCTGGAGGTGTCGTACCGCGTGCTCCGCCACCTCGCCCAGC

CC

SEQ ID NO: 29
MODC wild type sequence (mouse ornithine
decarboxylase)
CAGAGCCATGGCTTCCCGCCGGAGGTGGAGGAGCAGGATGATGGCAC

GCTGCCCATGTCTTGTGCCCAGGAGAGCGGGATGGACCGTCACCCTG

CAGCCTGTGCTTCTGCTAGGATCAATGTG

SEQ ID NO: 30
MODC modified sequence:
AGTCTCACGGCTTCCCACCCGAGGTCGAGGAGCAGGATGATGGCACA

CTGCCCATGAGCTGTGCTCAGGAGTCTGGCATGGACAGACACCCCGC

TGCCTGTGCCAGTGCCAGGATCAATGTG TGA

Destabilized and sequence modified reporters:
EXAMPLES OF destabilized and modified REPORTER SEQUENCES:

SEQ ID NO: 31
MONTASTRAEA CAVERNOSA
ATGGGCGTGATCAAGCCCGACATGAAGATCAAGCTGCGGATGGAGGG

CGCCGTGAACGGCCACAAATTCGTGATCGAGGGCGACGGGAAAGGCA

AGCCCTTCGAGGGCAAGCAGACCGATGGACCTGACCGTGATCGAGGG

CGCCCCCCTGCCCTTCGCCTACGACATCCTGACCACCGTGTTCGACT

ACGGCAACCGTGTCTTCGCCAAGTACCCCAAGGACATCCCTGACTAC

TTCAAGCAGACCTTCCCCGAGGGCTACTCGTGGGAGCGAAGCATGAC

ATACGAGGACCAGGGAATCTGCATCGCGACAAACGACATCACCATGA

TGAAGGGTGTGGACGACTGCTTCGTGTACAAAATCCGCTTCGACGGG

GTCAACTTCCCTGCCAATGGCCCGGTGATGCAGCGCAAGACCCTGAA

GTGGGAGCCCAGCACCGAGAAGATGTACGTGCGGGACGGCGTCCTGA

AGGGCGATGTGAACATGGCACTGCTCCTGGAGGGAGGCGGCCACTAC

CGCTGCGACTTCAAGACCACCTACAAAGCCAAGAAGGTGGTGCAGCT

-continued

GCCCGACTACCACTTCGTGGACCACCGCATCGAGATCGTGAGCCACG

ACAAGGACTACAACAAAGTCAAGCTGTACGAGCACGCCGAAGCCCAC

AGCGGACTGCCCCGCCAGGCCGGCAGTCTCACGGCTTCCCACCCGAG

GTCGAGGAGCAGGATGATGGCACACTGCCCATGAGCTGTGCTCAGGA

GTCTGGCATGGACAGACACCCCGCTGCCTGTGCCAGTGCCAGGATCA

ATGTGTGA

Bold in MODC seqeuence.

SEQ ID NO: 32
Clavulariidae Clavularia-OM: MODIFIED
ATGGTGAGCAAGGGCGAGGAGACCACAATGGGCGTGATCAAGCCCGA

CATGAAGATCAAGCTGAAGATGGAGGGCAACGTGAATGGCCACGCCT

TCGTGATCGAGGGCGAGGGCGAGGGCAAGCCCTACGACGGCACCAAC

ACCATCAACCTGGAGGTGAAGGAGGGAGCCCCCCTGCCCTTCTCCTA

CGACATCCTGACCACCGCGTTCAGCTACGGCAACAGGGCCTTCACCA

AGTACCCCGACGACATCCCCAACTACTTCAAGCAGTCCTTCCCCGAG

GGCTACAGCTGGGAGCGCACCATGACCTTCGAGGACAAGGGCATCGT

GAAGGTGAAGTCCGACATCTCCATGGAGGAGGACTCCTTCATCTACG

AGATCCACCTCAAGGGCGAGAACTTCCCCCCCAACGGCCCCGTGATG

CAGAAGGAGACCACCGGCTGGGACGCCTCCACCGAGAAGGGATGTAC

GTGCGCGACGGCGTGCTGAAGGGCGACGTCAAGATTGAAGCTGCTGC

TGGAGGGCGGCGGCCACCACCGCGTGGACTTCAAGACCATCTACAGG

GCCAAGAAGGCCGGTGAAGCTGCCCGACTATCACTTCGTGGACCACC

GCATCGAGATCCTGAACCACGACAAGGACTACAACAAGGTGACCGTG

TACGAGATCGCCGTGGCCCGCAACTCCACCGACGGCATGGACGAGCT

GTACAAGAGTCTCACGGCTTCCCACCCGAGGTCGAGGAGCAGGATG

ATGGCACACTGCCCCATGAGCTGTGCTCAGGAGTCTGGCATGGACAG

ACACCCCGCTGCCTGTGCCAGTGCCAGGATCAATGTG TGA

SEQ ID NO: 33
Firefly LUC + DU (Superluciferase):
ATGGAAGACGCCAAAAACATCAAGAAAGGCCCGGCGCCATTCTACCC

GCTGGAAGATGGAACCGCTGGAGAGCAACTGCACAAGGCCATGAAGA

GATACGCCCTGGTGCCTGGAACAATCGCGTTCACAGATGCACACATC

GAGGTGGACATCACCTACGCTGAGTACTTCGAAATGTCCGTCCGGCT

GGCAGAAGCCATGAAACGATACGGGCTGAACACAAATCACAGAATCG

TCGTGTGCAGTGAAAACTCTCTGCAATTCTTCATGCCGGTGCTGGGC

GCGCTGTTCATCGGAGTGGCAGTCGCGCCCGCGAACGACATCTACAA

TGAACGTGAACTCCTCAACAGCATGGGCATCTCGCAGCCCACCGTGG

TGTTCGTGTCCAAAAAGGGGCTGCAAAAAATCCTGAACGTGCAAAAA

AAGCTCCCAATCATCCAAAAAATCATCATCATGGACAGCAAAACGGA

CTACCAGGGATTCCAGTCGATGTACACGTTCGTCACATCTCATCTGC

CTCCCGGCTTCAATGAATAACGACTTCGTGCCAGAGTCCTTCGACAG

GGACAAGACAATCGCACTGATCATGAACTCCTCTGGAAGCACTGGTC

-continued

TGCCCAAAGGTGTCGCTCTGCCTCACAGAACTGCCTGCGTGAGATTC

TCGCATGCCAGAGATCCCATCTTCGGCAATCAAATCATCCCGGACAC

TGCGATCCTGAGTGTGGTCCCATTCCATCACGGCTTCGGAATGTTCA

CGACACTCGGATACCTGATCTGTGGATTCCGAGTCGTCCTGATGTAC

AGATTCGAAGAAGAGCTGTTCCTGAGGAGCCTCCAGGACTACAAGAT

CCAAAGTGCGCTGCTGGTGCCAACCCTGTTCTCCTTCTTCGCCAAAA

GCACTCTGATCGACAAATACGATCTCAGCAATCTGCACGAAATCGCC

TCTGGTGGCGCTCCCCTCTCCAAGGAAGTCGGGGAAGCGGTCGCCAA

GAGGTTCCATCTGCCAGGGATCAGGCAAGGATACGGGCTCACTGAGA

CGACATCAGCCATCCTGATCACACCCGAGGGGGATGACAAACCGGGC

GCGGTCGGGAAAGTGGTCCCCATTCTTCGAAGCGAAGGTTGTGGATC

TGGACACCGGGAAAACGCTGGGCGTTAATCAAAGAGGCGAACTGTGT

GTGAGAGGTCCCATGATCATGTCCGGCTACGTGAACAATCCGGAAGC

GACCAACGCCCTGATCGACAAGGATGGATGGCTCCACTCTGGAGACA

TCGCGTACTGGGACGAAGACGAACACTTCTTCATCGTGGACCGCCTG

AAGTCTCTGATCAAGTACAAAGGCTACCAGGTGGCTCCCGCTGAACT

CGAATCCATCCTGCTCCAACACCCCAACATCTTCGACGCAGGTGTCG

CAGGTCTGCCCGACGATGACGCCGGTGAACTGCCCGCCGCCGTCGTG

GTTCTGGAGCACGGAAAGACGATGACGGAAAAAGAGATCGTGGACTA

CGTCGCCAGTCAAGTAACAACCGCGAAAAAGCTGCGCGGAGGAGTTG

TGTTCGTGGACGAAGTGCCGAAAGGTCTGACCGGAAAACTCGACGCA

AGAAAAATCAGAGAGATCCTCATCAAGGCCAAGAAGGGCGGAAAGAT

CGCCGTGAGTCTCACGGCTTCCCACCCGAGGTCGAGGAGCAGGATGA

TGGCACACTGCCCATGAGCTGTGCTCAGGAGTCTGGCATGGACAGAC

ACCCCGCTGCCTGTGCCAGTGCCAGGATCAATGTG TGA

SEQ ID NO: 34
Firefly LUC2OM: LUC2 modified SuperLuciferase2
ATGGAAGATGCCAAAAACATCAAGAAGGGCCCAGCGCCATTCTACCC

ACTCGAAGACGGGACCGCAGGCGAGCAGCTGCACAAAGCCATGAAGC

GCTACGCCCTGGTGCCCGGCACCATCGCCTTCACCGACGCACACATC

GAGGTGGACATCACCTACGCCGAGTACTTCGAGATGAGCGTGCGGCT

GGCAGAAGCCATGAAGCGCTACGGGCTGAACACAAACCATCGGATCG

TGGTGTGCAGCGAGAACAGCCTGCAGTTCTTCATGCCCGTGCTGGGT

GCCCTGTTCATCGGTGTGGCTGTGGCCCCAGCCAACGACATCTACAA

CGAGCGCGAGCTGCTGAACAGCATGGGCATCAGCCAGCCCACCGTCG

TGTTCGTGAGCAAGAAAGGGCTGCAAAAGATCCTCAACGTGCAAAAG

AAGCTGCCGATCATCCAAAAGATCATCATCATGGACAGCAAGACCGA

CTACCAGGGCTTCCAAAGCATGTACACCTTCGTGACCTCCCACCTGC

CACCCGGCTTCAACGAGTACGACTTCGTGCCCGAGAGCTTCGACCGG

GACAAAACCATCGCCCTGATCATGAACAGCAGTGGCAGCACCGGACT

GCCCAAGGGCGTGGCACTGCCGCACCGCACCGCCTGTGTCCGATTCA

GTCATGCACGCGACCCCATCTTCGGCAACCAGATCATCCCCGACACC

-continued
GCCATCCTCAGCGTGGTGCCATTCCACCACGGCTTCGGCATGTTCAC
CACGCTGGGCTACTGGATCTGCGGCTTCCGGGTCGTGCTCATGTACC
GCTTCGAGGAGGAGCTGTTCCTGCGCAGCCTGCAAGACTACAAGATC
CAATCTGCCCTGCTGGTGCCCACACTGTTCAGCTTCTTCGCCAAGAG
CACTCTCATCGACAAGTACGACCTGAGCAACCTGCACGAGATCGCCA
GCGGCGGAGCGCCGCTCAGCAAGGAGTGGGTGAGGCCGTGGCCAAAC
GCTTCCACCTGCCAGGCATCCGCCAGGGCTACGGCCTGACAGAAACA
ACCAGCGCCATTCTGATCACCCCCGAAGGGGACGACAAGCCTGGCGC
AGTGGGCAAGGTGGTGCCCTTCTTCGAGGCCAAGGTGGTGGACCTGG
ACACCGGCAAGACACTGGGTGTGAACCAGCGCGGCGAGCTGTGCGTC
CGTGGCCCCATGATCATGAGCGGCTACGTGAACAACCCCGAGGCCAC
AAACGCTCTCATCGACAAGGACGGCTGGCTGCACAGCGGCGACATCG
CCTACTGGGACGAGGACGAGCACTTCTTCATCGTGGACCGGCTGAAG
AGCCTGATCAAATACAAGGGCTACCAGGTGGCCCCAGCCGAACTGGA
GAGCATCCTGCTGCAACACCCCAACATCTTCGACGCCGGAGTCGCCG
GACTGCCAGACGACGATGCCGGCGAGCTGCCCCGCAGCAGTCGTCGT
GCTGGAAACACGGCAAAACCATGACCGAGAAGGAGATCGTGGACTAC
GTGGCCAGCCAGGTGACAACCGCCAAGAAGCTGCGCGGTGGTGTGGT
GTTCGTGGACGAGGTGCCCAAAGGACTGACCGGCAAGCTGGACGCCC
GCAAGATCCGCGAGATCCTCATCAAGGCCAAGAAGGGCGGCAAGATC
GCCGTGAGTCTCACGGCTTCCCACCCGAGGTCGAGGAGCAGGATGAT
GGCACACTGCCCATGAGCTGTGCTCAGGAGTCTGGCATGGACAGACA
CCCCGCTGCCTGTGCCAGTGCCAGGATCAATGTG TGA

SEQ ID NO: 35
Puntellina Plumate GFP: modified sequences
ATGGAGAGCGACGAGAGCGGCCTGCCCGCCATGGAGATCGAGTGCCG
CATCACCGGCACCCTGAACGGCGTGGAGTTCGAGCTGGTGGGCGGCG
GAGAGGGCACCCCCGAGCAGGGCCGCATGACCAACAAGATGAAGAGA
CACCAAAGGCGCCCTGACCTTCAGCCCCTACCTGCTGAGCCACGTGA
TGGGCTACGGCTTCTACCACTTCGGCACCTACCCCAGCGGCTACGAG
AACCCCTTCCTGCACGCCATCAACAACGGCGGCTACACCAACACCCG
CATCGAGAAGTACGAGGACGGCGGCGTGCTGCACGTGTAGCTTCAGC
TACCGCTACGAGGCCGGCCGCGTGATCGGCGACTTCAAGGTGATGGG
CACCGGCTTCCCCGAGGACAGCGTGATCTTCACCGACAAGATCATCC
GCAGCAACGCCACCGTGGAGCACCTGCACCCCCATGGGCGACAACGA
CCTGGATGGCAGCTTCACCCGCACCTTCAGCCTGCGCGACGGCGGCT
ACTACAGCTCCGTGGTGGACAGCCACATGCACTTCAAGAGCGCCATC
CACCCCAGCATCCTGCAGAACGGGGGCCCCATGTTCGCCTTCCGCCG
CGTGGAGGAGGATCACAGCAACACCGAGCTGGGCATCGTGGAGTACC
AGCACGCCTTCAAGACDCCCGGATGCAGATGCCGGTGAAGAACAGTC
TCACGGCTTCCCACCCGAGGTCGAGGAGCAGGATGATGGCACACTGC

-continued
CCATGAGCTGTGCTCAGGAGTCTGGCATGGACAGACACCCCGCTGCC
TGTGCCAGTGCCAGGATCAATGTG TGA

SEQ ID NO: 36
Red Fluorescent protein modified sequence
ATGAGCGAGCTGATCAAGGAGAACATGCACATGAAGCTGTAATGGAG
GGCACCGTGAACAACCACCACTTCAAGTGCACATCCGAGGGCGAAGG
CAAGCCCTACGAGGGCACCCAGACCATGAAGATCAAGGTGGTCGAGG
GCGGCCCACTCCCCTTCGCCTTCGACATCCTGGCCACCAGCTTCATG
TACGGCAGCAAAGCCTTCATCAACCACACCCAGGGCATCCCCGACTT
CTTCAAGCAGTCCTTCCCTGAGGGCTTCACATGGGAGAGAATCACCA
CATACGAAGACGGGGCGTGCTGACCGCCACCCAGGACACCAGCTTC
CAGAACGGCTGCATCATCTACAACGTCAAGATCAACGGGGTGAACTT
CCCATCCAACGGCCCTGTGATGCAGAAGAAAACACGCGGCTGGGAGG
CCAACACCGAGATGCTGTACCCCGCTGACGGCGGCCTGAGAGGCCAC
AGCCAGATGGCCCTGAAGCTCGTGGGCGGGGCTACCTGCACTGCTC
CTTCAAGACCACATACAGATCCAAGAAACCCGCCAAGAACCTCAAGA
TGCCCGGCTTCCACTTCGTGGACCACAGACTGGAAAGAATCAAGGAG
GCCGACAAAAGAGACCTACGTCGAGCAGCACGAGATGGCTGTGGCCA
AGTACTGCGACCTCCCAAGCAAACTGGGGCACAGACAGTCTCACGGC
TTCCCACCCGAGGTCGAGGAGCAGGATGATGGCACACTGCCCATGAG
CTGTGCTCAGGAGTCTGGCATGGACAGACACCCCGCTGCCTGTGCCA
GTGCCAGGATCAATGT TGA

EXAMPLE 4

In Vivo Analysis of UU/UA-Reduced EGFP (1) The modified EGFP sequence was custom synthesized by a gene synthesis company and supplied contained in a pUC19 vector with flanking SalI and BamHI sites. 10 μg of the vector were digested with 10 units of SaiI in a buffer containing 0.1 μg/ml BSA for 1 hr at 37° C., followed by digestion with BamHI in BamHI buffer for an additional hour at 37° C. The digested DNA was extracted using the phenol-chloroform method, followed by ethanol precipitation. The synthetic EGFP-coding region was ligated into an expression vector, which had a CMV promoter and a BGH 3'UTR and had been digested with the same restriction enzymes (SalI and XbaI) and purified by phenol-chloroform extraction, followed by ethanol precipitation. Cloning of the EGFP-DNA into the expression vector was performed using the following ligation reaction: 30 μg of digested vector DNA were mixed with 90 μg of digested EGFP-DNA in a 10 μl reaction containing T4 DNA ligase. The ligated products were used to transform DH5α competent E. coli cells followed by expansion of the resulting colonies in a bacterial culture medium. The recombinant DNA was extracted using a Qiagen plasmid purification kit (Qiagen, Germany). The sizes of the vectors harboring the inserts were verified using gel electrophoresis. The resultant expression vector with the modified UU/UA-reduced coding region along with a vector containing the wild type DNA were used for functional studies to confirm the expression of the encoded protein. HEK293 cells were grown at standard culture conditions (37° C., 5% $CO_2$) in DMEM medium supplemented with 10% FBS and antibiotics (Invitrogen). $2.5 \times 10^4$ cells per well in 96-well plates were transfected with 100 ng of the vector with the modified UU/UA-reduced coding region of EGFP or the vector containing the wild-type EGFP-DNA. Transfections were performed in serum-free medium using Lipofectamine 2000 (Invitrogen) for 5 h, followed by replacing the medium with serum-supplemented medium. After approximately 24 or 48 hours, the plates were imaged and quantified using a BD high-content imager. Quantification was performed with a Proxcell imaging algorithm.

The data clearly shows that the use of the UU/UA-reduced coding region of EGFP allows a significantly (2.5 to 3-fold) higher expression of EGFP in eukaryotic cells than that of the wild type EGFP-DNA (FIG. 1).

(2) HEK293 cells were grown at standard culture conditions (37° C., 5% $CO_2$) in DMEM medium supplemented with 10% FBS and antibiotics (Invitrogen). $2.5 \times 10^4$ cells per well in 96-well plates were transfected with 100 ng of the vector with the modified UU/UA-reduced coding region of EGFP or the vector containing the wild-type EGFP-DNA. The cells were also co-transfected with either an empty control vector (pcDNA 3.1) or a RNase L vector (pcDNA 3.1). Transfections were performed in serum-free medium using Lipofectamine 2000 (Invitrogen) for 5 h, followed by replacing the medium with serum-supplemented medium. After approximately 24 or 48 hours, the plates were imaged and quantified using a BD high-content imager. Quantification was performed with a Proxcell imaging algorithm.

Figure 2:
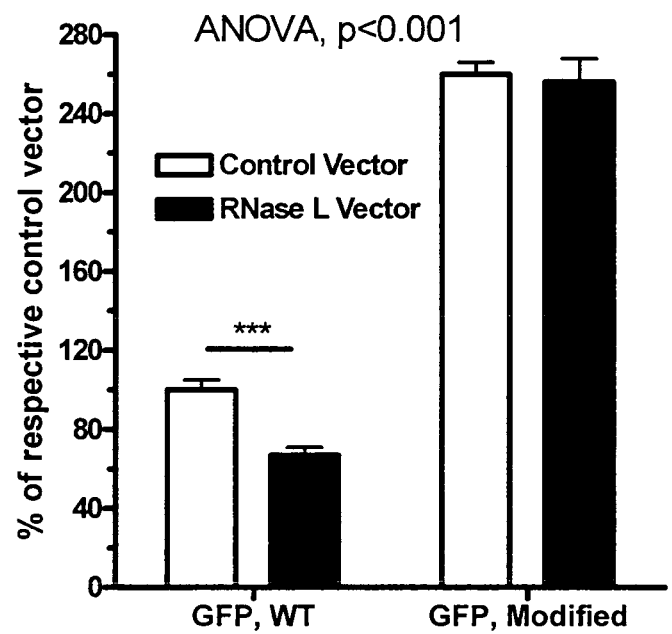

The data shows that—in comparison/contrast to the wild type EGFP sequence—the use of the modified EGFP sequence resulted in higher expression, which was not constrained by the co-expression of RNase L (FIG. 2).

(3) Expression active PCR products were generated by using primers in which the forward (5') primers were complementary to the beginning of the CMV promoter region or a sequence upstream of the CMV promoter, while the reverse (3') primers were complementary to the BGH poly A site or a sequence downstream of this site. The PCR was carried out using a mixture of Taq and Pfu polymerase in a 100 µl reaction with the following cycle conditions: —95° C. for 12 min (to activate hot start polymerases), —32 cycles of: 94° C., 1 min; 52° C., 1 min; 72° C., 4 min, and a final extension at 72° C. for 7 min. The PCR products were purified using Qiagen PCR purification columns to eliminate the primers, small PCR products, buffer, and enzymes, and eluted in sterile water. HEK293 cells were grown at standard culture conditions (37° C., 5% $CO_2$) in DMEM medium supplemented with 10% FBS and antibiotics (Invitrogen). $2.5 \times 10^4$ cells per well in 96-well plates were transfected with 100 ng of purified PCR products generated from the EGFP expression vector with the wild type or with the modified sequence. Transfections were performed in serum-free medium using Lipofectamine 2000 (Invitrogen) for 5 h, followed by replacing the medium with serum-supplemented medium. After approximately 24 or 48 hours, the plates were imaged and quantified using a BD high-content imager. Quantification was performed with a Proxcell imaging algorithm.

Figure 3:
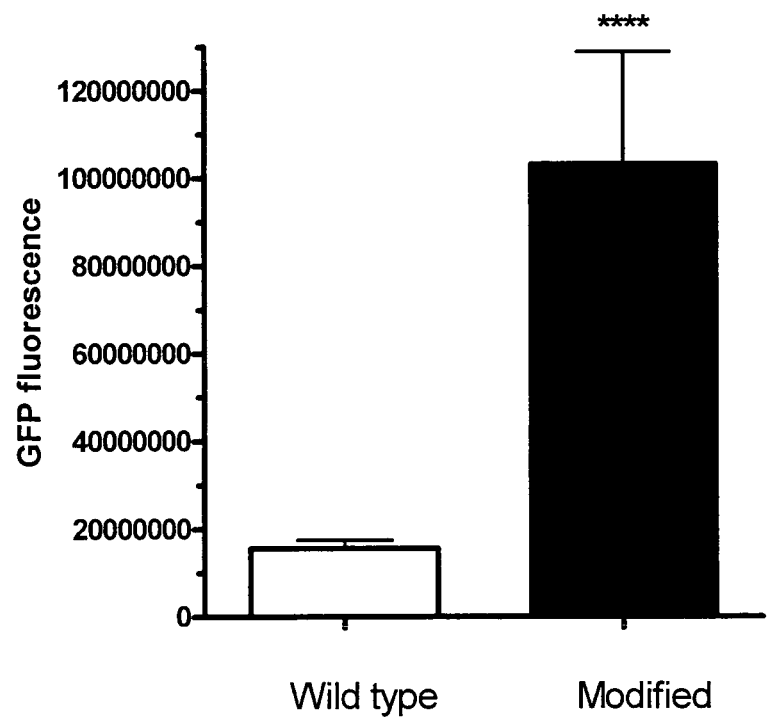

The data shows that PCR products harboring the UU/UA-reduced coding region of EGFP led to higher expression of EGFP (5 to 10-fold increase) than those harboring the wild type sequence (FIG. 3).

Figure 4:
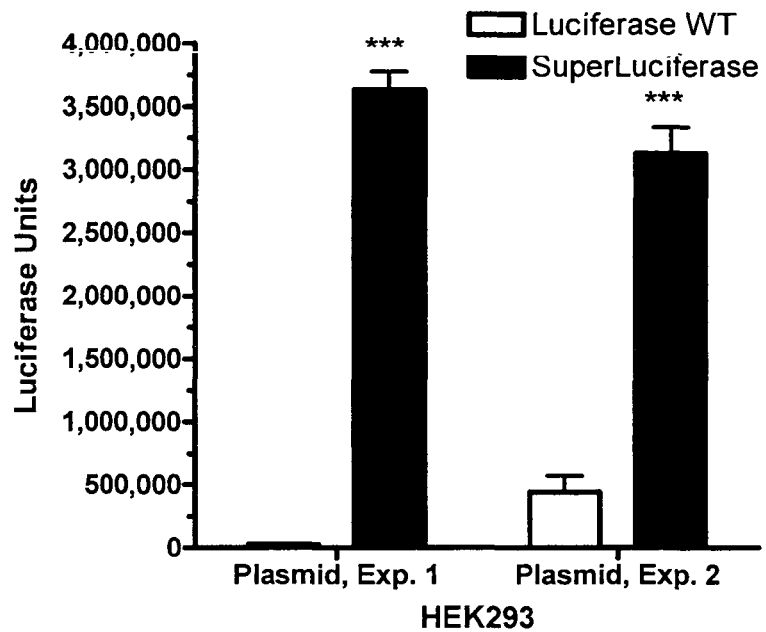
FIG. 4 is a graph showing luciferase activity in Hek293 cells transfected with either a wild type or modified (i.e. UU/AG-reduced) firefly luciferase expression vector.

(4) Using the same methodology as described in (2) and (3), Hek293 cells were transfected with wild type or UU/UA-reduced firefly luciferase expression vector ("Superluciferase", SEQ ID NO: 15). The luciferase activity levels were quantified by a luminometer. The data show that, within two independent experiments, there was an approximately 5- and approximately 100-fold difference (FIG. 4).

Figure 5:
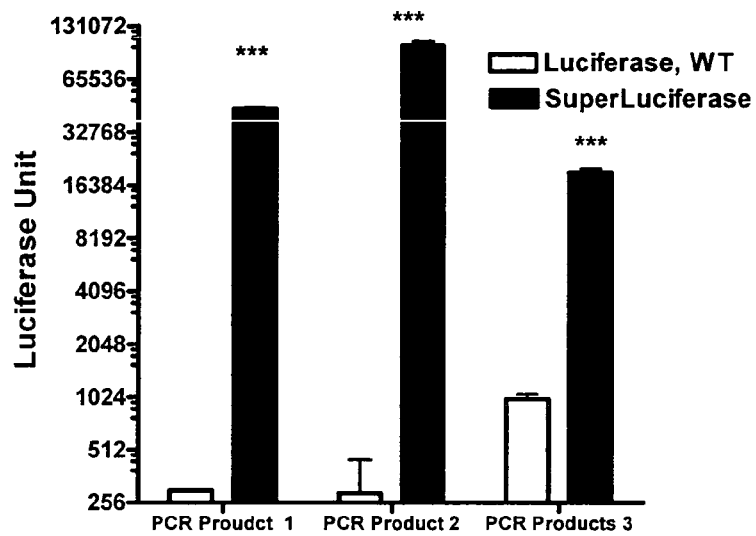
FIG. 5 is a graph showing luciferase activity in Huh7 cells which have been transfected with different PCR products generated from wild type or UU/UA-reduced firefly luciferase expression vector.

Likewise, Huh7 cells were transfected with different PCR products generated in accordance with the methodology outlined in (3) above, from the wild type or modified firefly luciferase expression vector ("Superluciferase"; SEQ ID NO: 15). The luciferase activity levels were, again, quantified by a luminometer. The data show that PCR products harbouring the UU/UA-reduced coding region of superluciferase led to a substantially higher expression of luciferase (20-100-fold increase) than those harbouring the wildtype sequence (FIG. 5). This demonstrates the method in accordance with the present invention works with a verity of variety of reporter proteins.

Figure 6:
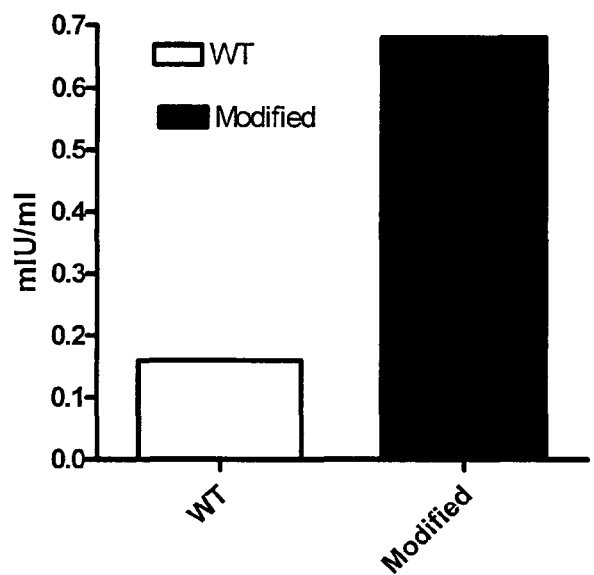
FIG. 6 is a graph showing expression of hepatitis B surface antigen in Hek293 cells transfected with a wild type or UU/UA-reduced hepatitis B surface antigen expression vector.

Likewise, Hek293 cells were transfected, using the same methodology as in (2), above, with a wild type or UU/UA-reduced hepatitis B surface (SEQ ID NO: 23) antigen expression vector. The expressed protein was quantified as mIU/ml. There was approximately a 4-fold difference (FIG. 6), but it is likely that this may be even higher in independent experiments.

This is an example that the method in accordance with the present invention also works with therapeutic proteins, antibodies and vaccines which have been modified, i.e. their coding sequence has been UU/UA-reduced, and this leads to a substantial increase in expression.

(5) In order to reflect the transcriptional changes and the subsequent effects on reported protein levels, protein-destabilizing amino acid regions that include a PEST sequence (=peptide sequence which is rich in proline, glutamic acid, serine and threonine) have been used to reduce the half-life of various reporter proteins. PEST sequences are associated with proteins that have a short intracellular half-life. Li et al. (J. Biol. Chem., 1998, 273, pp. 34970-34975) describe the use of a PEST sequence of MODC to destabilize the EGFP, and Leclerc et al. (Biotechniques, 2000, 29, pp. 590-591, pp. 594-596 used a PEST sequence to reduce the protein half-life of firefly luciferase.

Using such MODC-domain (mouse ornithine decarboxylase), more specifically, amino acids 422-461 of the degradation domain of the highly unstable MODC, the present inventor rendered a number of reporter genes unstable by fusing them with the afore-mentioned MODC domain. Moreover, the present inventor modified such fusions by reducing the number of UU/UA dinucleotides in both the reporter gene and the MODC domain in accordance with the present invention with respect to EGFP from Aequorea Victoria, Montastrea Cavernosa, Clavularia and Puntelina Plumate. The number of UU/UA dinucleotides was reduced both in the EGFP-part and the MODC part of the fusion.

Figure 7:
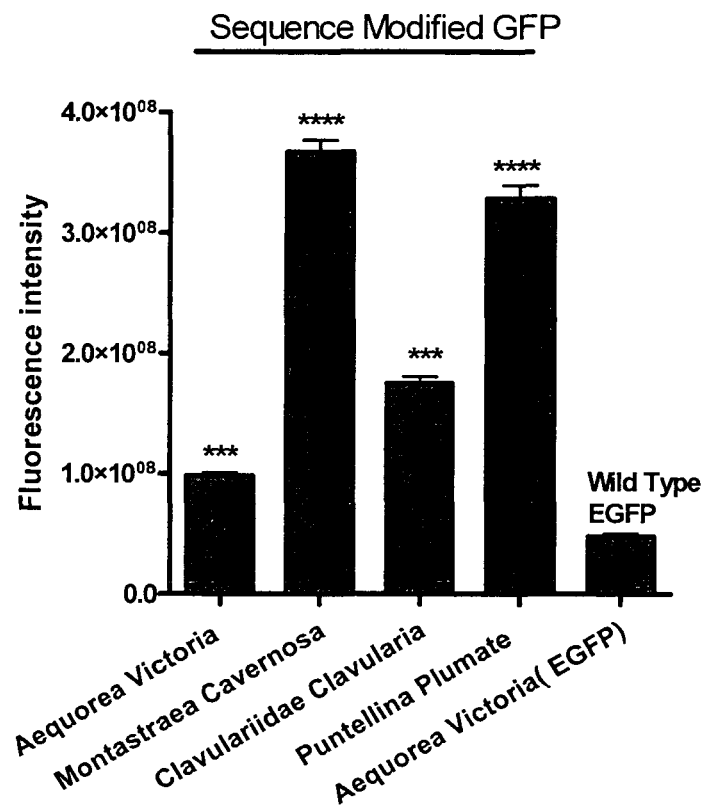
FIG. 7 is a graph showing expression of various green fluorescent proteins in Hek293 cells transfected with MODC-destabilized wildtype and MODC-destabilized UU/UA-reduced green fluorescent proteins.

The MODC domain was amplified from genomic DNA of mouse fibroblasts using specific primers that contain EcoRI and BamHI sites in the forward and reverse primer, respectively. The amplified cDNA was cloned in frame with the GFP coding region using the same restriction sites. Hek293 cells were transfected with destabilized GFPs as indicated in FIG. 7. The fluorescence intensity was quantitated by imaging apparatus and software. Compared to destabilized wildtype EGFP from Aequorea Victoria (i.e. the point of reference was wildtype EGFP, SEQ ID NO: 8, fused to wildtype MODC, SEQ ID NO: 29), there was a two-fold increase in fluorescence from modified Aequorea Victoria, an 8-fold increase from modified Montastrea Cavernosa green fluorescent protein, a 4-fold increase from modified Clavularia green fluorescent protein and a 7-fold increase from modified Puntelina Plumate green fluorescent protein (see FIG. 7). The term "modified" here means "UU/UA reduced and fused with MODC which itself has also been UU/UA reduced".

Consequently, this shows that the present invention also works in situations where expression signals normally are weaker, and improves the fold-increase in expression in such situations.

REFERENCES

Al-Zoghaibi F., T. Ashour, W. Al-Ahmadi, H. Abulleef, O. Demirkaya, and K. S. A. Khabar. 2007. Bioinformatics and experimental derivation of an efficient hybrid 3' untranslated region and use in expression active linear DNA with minimum poly(A) regions. *Gene* 391: 130-139.

Bakheet, T., B. R. Williams, and K. S. Khabar. 2006. ARED 3.0: the large and diverse AU-rich transcriptome. *Nucleic Acids Res* 34: D111-114.

Barreau, C., L. Paillard, and H. B. Osborne. 2005. AU-rich elements and associated factors: are there unifying principles? *Nucleic Acids Res* 33: 7138-7150.

Bisbal, C., M. Silhol, H. Laubenthal, T. Kaluza, G. Carnac, L. Milligan, F. Le Roy, and T. Salehzada. 2000. The 2'-5' oligoadenylate/RNase L/RNase L inhibitor pathway regulates both MyoD mRNA stability and muscle cell differentiation. *Mol Cell Biol* 20: 4959-4969.

Chandrasekaran, K., Z. Mehrabian, X. L. Li, and B. Hassel. 2004. RNase-L regulates the stability of mitochondrial DNA-encoded mRNAs in mouse embryo fibroblasts. *Biochem Biophys Res Commun* 325: 18-23.

Dong, B., M. Niwa, P. Walter, and R. H. Silverman. 2001. Basis for regulated RNA cleavage by functional analysis of RNase L and Ire1p. *Rna* 7: 361-373.

Foecking, M. K., and Hofstetter, H. 1986. Powerful and versatile enhancer-promoter unit for mammalian expression vectors. *Gene* 45: 101-105.

Han, J. Q., G. Wroblewski, Z. Xu, R. H. Silverman, and D. J. Barton. 2004. Sensitivity of hepatitis C virus RNA to the antiviral enzyme ribonuclease L is determined by a subset of efficient cleavage sites. *J Interferon Cytokine Res* 24: 664-76.

Hassel, B. A., A. Zhou, C. Sotomayor, A. Maran, and R. H. Silverman. 1993. A dominant negative mutant of 2-5A-dependent RNase suppresses antiproliferative and antiviral effects of interferon. *Embo J* 12: 3297-3304.

Khabar, K. S., Y. M. Siddiqui, F. al-Zoghaibi, L. al-Haj, M. Dhalla, A. Zhou, B. Dong, M. Whitmore, J. Paranj ape, M. N. Al-Ahdal et al. 2003a. RNase L mediates transient control of the interferon response through modulation of the double-stranded RNA-dependent protein kinase PKR. *J Biol Chem* 278: 20124-20132.

Khabar, K. S., Y. M. Siddiqui, F. al-Zoghaibi, L. al-Haj, M. Dhalla, A. Zhou, B. Dong, M. Whitmore, J. Paranjape, M. N. Al-Ahdal et al. 2003b. RNase L mediates transient control of the interferon response through modulation of the double-stranded RNA-dependent protein kinase PKR. *J Biol Chem* 278: 20124-20132.

Kobayashi, M., Tanaka, A., Hayashi, Y., and Shimamura, S. 1997. The CMV enhancer stimulates expression of foreign genes from the human EF-1 alpha promoter. *Anal Biochem* 247: 179-181.

Lai, W. S., J. S. Parker, S. F. Grissom, D. J. Stumpo, and P. J. Blackshear. 2006. Novel mRNA targets for tristetraprolin (TTP) identified by global analysis of stabilized transcripts in TTP-deficient fibroblasts. *Mol Cell Biol* 26: 9196-9208.

Lal, A., K. Mazan-Mamczarz, T. Kawai, X. Yang, J. L. Martindale, and M. Gorospe. 2004. Concurrent versus individual binding of HuR and AUF1 to common labile target mRNAs. *Embo J* 23: 3092-3102.

Legendre M, Gautheret D. 2003 Sequence determinants in human polyadenylation site selection. *BMC Genomics.* 4: 7.

Le Roy, F., C. Bisbal, M. Silhol, C. Martinand, B. Lebleu, and T. Salehzada. 2001. The 2-5A/RNase L/RNase L inhibitor (RLI) [correction of (RNI)] pathway regulates mitochondrial mRNAs stability in interferon alpha-treated H9 cells. *J Biol Chem* 276: 48473-48482.

Li, X., J. A. Blackford, and B. A. Hassel. 1998a. RNase L Mediates the Antiviral Effect of Interferon through a Selective Reduction in Viral RNA during Encephalomyocarditis Virus Infection. *Journal of Virology* 72: 2752-2759.

Li, X., X. Zhao, Y. Fang, X. Jiang, T. Duong, C. Fan, C. C. Huang, and S. R. Kain. 1998b. Generation of destabilized green fluorescent protein as a transcription reporter. *J Biol Chem* 273: 34970-34975.

Li, X. L., J. A. Blackford, C. S. Judge, M. Liu, W. Xiao, D. V. Kalvakolanu, and B. A. Hassel. 2000. RNase-L-dependent destabilization of interferon-induced mRNAs. A role for the 2-5A system in attenuation of the interferon response. *J Biol Chem* 275: 8880-8888.

Lopez de Silanes, I., S. Galban, J. L. Martindale, X. Yang, K. Mazan-Mamczarz, F. E. Indig, G. Falco, M. Zhan, and M. Gorospe. 2005. Identification and functional outcome of mRNAs associated with RNA-binding protein TIA-1. *Mol Cell Biol* 25: 9520-9531.

Naylor, L. H. 1999. Reporter gene technology: the future looks bright. *Biochem Pharmacol* 58: 749-757.

Wrechester, D. H., J. W. McCauley, J. J. Skehel, and I. M. Kerr. 1981. Interferon action: sequence specificity of the ppp(A2'p)nA-dependent ribonuclease. *Nature* 289: 414-7.

Wreschner, D. H., James, T. C., Silverman, R. H., and Kerr, I. M. (1981). *Nucleic Acids Res* 9: 1571-1581.

Zhao, S., S. L. Ooi, and A. B. Pardee. 1995. New primer strategy improves precision of differential display. *Biotechniques* 18: 842-846, 848, 850.

Zhou, A., J. Paranjape, T. L. Brown, H. Nie, S, Naik, B. Dong, A. Chang, B. Trapp, R. Fairchild, C. Colmenares et al. 1997. Interferon action and apoptosis are defective in mice devoid of 2',5'-oligoadenylate-dependent RNase L. *Embo J* 16: 6355-6363.

The invention claimed is:

1. A method for increasing the expression of a protein in a cell, said method comprising the step of reducing the number of RNase L cleavage sites in a nucleic acid sequence encoding said protein, and wherein the cell is a eukaryotic cell.

2. The method according to claim 1, wherein the number of RNase L cleavage sites is reduced by at least 10%.

3. The method according to claim 1, wherein said cleavage sites are UU and/or UA dinucleotides.

4. The method according to claim 1, wherein the step of reducing the number of RNase L cleavage sites reduces the number of said sites in a coding region of said nucleic acid sequence.

5. The method according to claim 4, wherein the step of reducing the number of RNase L cleavage sites in said nucleic acid sequence is performed without altering the amino acid sequence of said protein.

6. The method according to claim 5, wherein in the step of reducing the number of RNase L cleavage sites a codon comprising a UU and/or UA dinucleotide is exchanged for an alternative codon not comprising a UU and/or UA dinucleotide and coding for the same amino acid.

7. The method according to claim 5, wherein in the step of reducing the number of RNase L cleavage sites at least one codon of an adjacent pair of codons comprising a UU and/or UA dinucleotide is exchanged for an alternative codon coding for the same amino acid so that said adjacent pair of codons no longer comprises a UU and/or UA dinucleotide.

8. The method according to claim 6, wherein said alternative codon is a more frequently used codon in said cell.

9. The method according to claim 1, wherein the step of reducing the number of RNase L cleavage sites reduces said number in a non-coding region of said nucleic acid sequence.

10. The method according to claim 9, wherein said non-coding region is a 5'UTR, a 3'UTR, or an intron.

11. The method according to claim 9, wherein the step of reducing the number of RNase L cleavage sites is performed by mutation, deletion, or insertion of one or more nucleotides.

12. The method according to claim 1, further comprising the step of codon optimization prior to the step of reducing the number of RNase L cleavage sites.

13. The method according to claim 1, further comprising the step of transfecting said nucleic acid sequence encoding said protein into said cell in an expression active PCR product or contained in an expression vector after the step of reducing the number of RNase L cleavage sites.

14. The method according to claim 13, further comprising the step of translating said protein from said expression active PCR product or expression vector in said cell.

15. The method according to claim 1, wherein said protein is selected from the group consisting of reporter proteins, therapeutic proteins, antibodies, vaccines, membrane proteins, fusion proteins, blood plasma proteins, cytokines, interferons, growth factors, chemokines, and GPCRs.

* * * * *

UNITED STATES PATENT AND TRADEMARK OFFICE
CERTIFICATE OF CORRECTION

PATENT NO. : 8,790,896 B2
APPLICATION NO. : 13/144621
DATED : July 29, 2014
INVENTOR(S) : Khalid S. Khabar It is certified that error appears in the above-identified patent and that said Letters Patent is hereby corrected as shown below:

In the Specification

Column 11,
Lines 16-17, "Alanine (A) UNN" should read --Alanine (A) ANN--.

Column 17,
Line 46, "CACATCAA" should read --CACCATCAA--.

Column 18,
Line 26, "AAGGTACCG" should read --AAGGTGACCG--.

Column 19,
Line 24, "CACAGATCGT" should read --CACAGAATCGT--.

Column 21,
Line 51, "ACACGCGGCG" should read --ACAGCGGCG--.

Column 22,
Line 40, "CTTCAT" should read --CTTCAG--.

Column 22,
Line 52, "GGAGATA" should read --GGAGTA--.

Column 23,
Line 28, "ACCGCACCC" should read --ACCGCCACCC--.

Column 23,
Line 52, "TATTCGCTGG" should read --TATCGCTGG--.

Signed and Sealed this
Twenty-fourth Day of February, 2015

Michelle K. Lee
*Deputy Director of the United States Patent and Trademark Office*

Column 25,
Line 40, "ATGA" should read --TGA--.

Column 25,
Line 44, "GGACCCT" should read --GGACCT--.

Column 25,
Line 53, "CTCGGG" should read --CTGGG--.

Column 26,
Line 10, "GGGCGAT" should read --GGCGAT--.

Column 26,
Line 10, "GCCAG" should read --GCAG--.

Column 26,
Line 52, "AGACCGA" should read --AGACGA--.

Column 27,
Line 30, "GAGAAGGG" should read --GAGAGG--.

Column 27,
Line 32, "GATTGAA" should read --GATGAA--.

Column 27,
Line 35, "GGCCGG" should read --GGCGG--.

Column 27,
Line 64, "TAACGAC" should read --TACGAC--.

Column 29,
Line 10, "GGAGTGGG" should read --GGAGGTGGG--.

Column 29,
Line 29, "GGAAACA" should read --GGAACA--.

Column 29,
Lines 44-45, "AAGAGACA" should read --AAGAGCA--.

Column 29,
Line 50, "CGTGTAGCTT" should read --CGTGAGCTT--.

Column 29,
Line 55, "ACCCCCA" should read --ACCCCA--.

Column 29,
Line 64, "ACDCCCGG" should read --ACCCCGG--.

Column 30,
Line 7, "CTGTAATGG" should read --CTGTACATGG--.

Column 30,
Line 28, "CAAAAG" should read --CAAAG--.

Column 30,
Line 34, "TGT TGA" should read --TGTG TGA--.

Column 30,
Line 44, "of Sail" should read --of SalI--.

UNITED STATES PATENT AND TRADEMARK OFFICE
CERTIFICATE OF CORRECTION

Page 1 of 1

PATENT NO. : 8,790,896 B2
APPLICATION NO. : 13/144621
DATED : July 29, 2014
INVENTOR(S) : Khalid S. Khabar It is certified that error appears in the above-identified patent and that said Letters Patent is hereby corrected as shown below:

In the Specification

Column 14,
Line 56, delete

"GGTGAGGCCGAGTTTGGTAAGTGTCCTCTGAACAGCACAACTGAATG"

insert

--GGTGAGGCCGAGTTTGGTAAGTGTCCTCTGAACAGCACAACTGAATGAGACAGA--.

Signed and Sealed this
Seventh Day of April, 2015

Michelle K. Lee
*Director of the United States Patent and Trademark Office*

SEQUENCE LISTING

<160> NUMBER OF SEQ ID NOS: 36

<210> SEQ ID NO 1
<211> LENGTH: 175
<212> TYPE: DNA
<213> ORGANISM: Oryctolagus cuniculus

<400> SEQUENCE: 1

```
ggtgaggccg agtttggtaa gtatccttt tacagcacaa cttaatgaga cagatagaaa      60
ctgaccggtg ggagtctgcg gccgcagtct tgtagaaaca gagtagtcgc ctgcttttct    120
gccaggtgct gacttctctc cccttctctt ttttcctttt ctcaggttgg tgtcg          175

<210> SEQ ID NO 2
<211> LENGTH: 173
<212> TYPE: DNA
<213> ORGANISM: Artificial Sequence
<220> FEATURE:
<223> OTHER INFORMATION: Reduced number of UU and/or UA dinucleotides

<400> SEQUENCE: 2
ggtgaggccg agtttggtaa gtgtcctctg aacagcacaa ctgaatgaga cagaagaaac     60
tgaccggtgg gagtctgcgg ccgcagtctg tagaaacaga gtagtcgcct gcttttctgc   120
caggtgctga cttctctccc cttctctttt tccttttct caggttggtg tcg             173

<210> SEQ ID NO 3
<211> LENGTH: 173
<212> TYPE: DNA
<213> ORGANISM: Artificial Sequence
<220> FEATURE:
<223> OTHER INFORMATION: Reduced number of UU and/or UA dinucleotides

<400> SEQUENCE: 3
ggtgaggccg agtttggtaa gtgtcctctg aacagcacaa ctgaatgaga cagaagaaac     60
tgaccggtgg gagtctgcgg ccgcagtctg tagaaacaga gtagtcgcct gtcttctgcc   120
aggtgctgac tctctctccc cttctctctc ttcctcttct caggttggtg tcg            173

<210> SEQ ID NO 4
<211> LENGTH: 126
<212> TYPE: DNA
<213> ORGANISM: Simian virus 40

<400> SEQUENCE: 4
tgaatgcaat tgttgttgtt aacttgttta ttgcagctta taatggttac aaataaagca     60
atagcatcac aaatttcaca aataaagcat ttttttcact gcattctagt tgtggtttgt   120
ccaaac                                                                 126

<210> SEQ ID NO 5
<211> LENGTH: 118
<212> TYPE: DNA
<213> ORGANISM: Artificial Sequence
<220> FEATURE:
<223> OTHER INFORMATION: Reduced number of UU and/or UA dinucleotides

<400> SEQUENCE: 5
tgaatgcaat gtgcgtcaac tgtctgtctg cagctcacaa tggttacaaa taaagcaatg     60
catcacaaat ctcacaaatc aagcatctgt cactgcatct agtgtggtct gtccaaac      118

<210> SEQ ID NO 6
<211> LENGTH: 245
<212> TYPE: DNA
<213> ORGANISM: Bos taurus

<400> SEQUENCE: 6
tctagagatc tgtgtgttgg ttttttgtgg atctgctgtg ccttctagtt gccagccatc     60
tgttgtttgc ccctcccccg tgccttcctt gaccctggaa ggtgccactc ccactgtcct   120
ttcctaataa aatgaggaaa ttgcatcgca ttgtctgagt aggtgtcatt ctattctggg   180
```

```
gggtggggtg gggcagcaca gcaagggga ggattgggaa gacaatagca ggcatgctgc    240
ttaag                                                                245

<210> SEQ ID NO 7
<211> LENGTH: 237
<212> TYPE: DNA
<213> ORGANISM: Artificial Sequence
<220> FEATURE:
<223> OTHER INFORMATION: Reduced number of UU and/or UA dinucleotides

<400> SEQUENCE: 7
tctagagatc tgtgtgttgg tctgtgtgga tctgctgtgc ctctagtgcc agccatctgt    60
gtctgcccct cccccgtgcc tcctgaccct ggaaggtgcc actcccactg tcctgtccta   120
ataaaatgag gaaatgcatc gcatgtctga gtggtgtcat ctctatcctg ggggtgggg   180 tggggcagca cagcaagggg gaggatctgg gaagacaatg caggcatgct gcttaag      237

<210> SEQ ID NO 8
<211> LENGTH: 717
<212> TYPE: DNA
<213> ORGANISM: Artificial Sequence
<220> FEATURE:
<223> OTHER INFORMATION: Enhanced green fluorescent protein

<400> SEQUENCE: 8
atggctagca aaggagaaga actcttcact ggagttgtcc caattcttgt tgaattagat    60
ggtgatgtta acggccacaa gttctctgtc agtggagagg gtgaaggtga tgcaacatac   120
ggaaaactta ccctgaagtt catctgcact actggcaaac tgcctgttcc atggccaaca   180
ctagtcacta ctctgtgcta tggtgttcaa tgcttttcaa gatacccgga tcatatgaaa   240
cggcatgact tttttcaagag tgccatgccc gaaggttatg tacaggaaag gaccatcttc   300
ttcaaagatg acggcaacta caagacacgt gctgaagtca agtttgaagg tgataccctt   360
gttaatagaa tcgagttaaa aggtattgac ttcaaggaag atggcaacat tctgggacac   420
aaattggaat acaactataa ctcacacaat gtatacatca tggcagacaa acaaaagaat   480
ggaatcaaag tgaacttcaa gacccgccac aacattgaag atggaagcgt tcaactagca   540
gaccattatc aacaaaatac tccaattggc gatggccctg tccttttacc agacaaccat   600
tacctgtcca cacaatctgc cctttcgaaa gatcccaacg aaaagagaga ccacatggtc   660
cttcttgagt ttgtaacagc tgctgggatt acacatggca tggatgaact gtacaac      717

<210> SEQ ID NO 9
<211> LENGTH: 717
<212> TYPE: DNA
<213> ORGANISM: Artificial Sequence
<220> FEATURE:
<223> OTHER INFORMATION: Reduced number of UU and/or UA dinucleotides

<400> SEQUENCE: 9
atggccagca agggcgagga actgttcacc ggcgtggtgc ccatcctggt ggagctggac    60
ggcgacgtga acggccacaa gttcagcgtg agcggcgagg gcgaaggcga cgccacctac   120
ggcaagctga ccctgaagtt catctgcacc accggcaagc tgcccgtgcc ctggcccacc   180
ctggtgacca ccctgtgcta cggcgtgcag tgcttcagca gatacccga ccacatgaag   240 cggcacgact tcttcaagag cgccatgccc gagggctacg tgcaggaacg gaccatcttc   300
ttcaaggacg acggcaacta caagaccagg gccgaggtga agttcgaggg cgacacactg   360
```

```
gtgaaccgga tcgagctgaa gggcatcgac ttcaaagagg acggcaacat cctgggccac      420
aagctggaat acaactacaa cagccacaac gtgtacatca tggccgacaa gcagaagaac      480
ggcatcaagg tcaacttcaa gacccggcac aacatcgagg acggcagcgt gcagctggcc      540
gaccactacc agcagaacac ccccatcggc gacggccccg tgctgctgcc cgacaaccac      600
tacctgagca cccagagcgc cctgagcaag gaccccaacg agaagcggga ccacatggtg      660
ctgctggaat cgtgacagc cgccggaatc acccacggca tggacgagct gtacaac         717
```

<210> SEQ ID NO 10
<211> LENGTH: 684
<212> TYPE: DNA
<213> ORGANISM: Montastrea cavernosa

<400> SEQUENCE: 10

```
atgggcgtga tcaagcccga catgaagatc aagctgcgga tggagggcgc cgtgaacggc       60
cacaaattcg tgatcgaggg cgacgggaaa ggcaagccct ttgagggtaa gcagactatg      120
gacctgaccg tgatcgaggg cgccccctg cccttcgctt atgacattct caccaccgtg      180
ttcgactacg gtaaccgtgt cttcgccaag taccccaagg acatccctga ctacttcaag      240
cagaccttcc ccgagggcta ctcgtgggag cgaagcatga catacgagga ccagggaatc      300
tgtatcgcta caaacgacat caccatgatg aagggtgtgg acgactgctt cgtgtacaaa      360
atccgcttcg acggggtcaa cttccctgct aatggcccgg tgatgcagcg caagaccctg      420
aagtgggagc ccagtaccga gaagatgtac gtgcgggacg cgtactgaa gggcgatgtt      480 aatatggcac tgctcttgga gggaggcggc cactaccgct cgacttcaa gaccacctac      540 aaagccaaga aggtggtgca gcttcccgac taccattcg tggaccaccg catcgagatc      600
gtgagccacg acaaggacta caacaaagtc aagctgtacg agcacgccga agcccacagc      660
ggactacccc gccaggccgg ctaa                                             684
```

<210> SEQ ID NO 11
<211> LENGTH: 809
<212> TYPE: DNA
<213> ORGANISM: Artificial Sequence
<220> FEATURE:
<223> OTHER INFORMATION: Reduced number of UU and/or UA dinucleotides

<400> SEQUENCE: 11

```
atgggcgtga tcaagcccga catgaagatc aagctgcgga tggagggcgc cgtgaacggc       60
cacaaattcg tgatcgaggg cgacgggaaa ggcaagccct tcgagggcaa gcagacgatg      120
gacctgaccg tgatcgaggg cgccccctg cccttcgcct acgacatcct gaccaccgtg      180
ttcgactacg gcaaccgtgt cttcgccaag taccccaagg acatccctga ctacttcaag      240
cagaccttcc ccgagggcta ctcgtgggag cgaagcatga catacgagga ccagggaatc      300
tgcatcgcga caaacgacat caccatgatg aagggtgtgg acgactgctt cgtgtacaaa      360
atccgcttcg acggggtcaa cttccctgcc aatggcccgg tgatgcagcg caagaccctg      420
aagtgggagc ccagcaccga gaagatgtac gtgcgggacg cgtcctgaa gggcgatgtg      480 aacatggcac tgctcctgga gggaggcggc cactaccgct cgacttcaa gaccacctac      540 aaagccaaga aggtggtgca gctgcccgac taccattcg tggaccaccg catcgagatc      600
gtgagccacg acaaggacta caacaaagtc aagctgtacg agcacgccga agcccacagc      660
ggactgcccc gccaggccgg ctgaagtctc acggcttccc acccgaggtc gaggagcagg      720
atgatggcac actgcccatg agctgtgctc aggagtctgg catggacaga caccccgctg      780
```
cctgtgccag tgccaggatc aatgtgtga                               809

<210> SEQ ID NO 12
<211> LENGTH: 711
<212> TYPE: DNA
<213> ORGANISM: Clavularia species

<400> SEQUENCE: 12
atggtgagca agggcgagga gaccacaatg ggcgtaatca agcccgacat gaagatcaag    60
ctgaagatgg agggcaacgt gaatggccac gccttcgtga tcgagggcga gggcgagggc   120
aagccctacg acggcaccaa caccatcaac ctggaggtga aggagggagc ccccctgccc   180
ttctcctacg acattctgac caccgcgttc agttacggca cagggcctt caccaagtac   240 cccgacgaca tccccaacta cttcaagcag tccttccccg agggctactc ttgggagcgc   300
accatgacct tcgaggacaa gggcatcgtg aaggtgaagt ccgacatctc catggaggag   360
gactccttca tctacgagat cacctcaag ggcgagaact ccccccaa cggcccgtg       420 atgcagaagg agaccaccgg ctgggacgcc tccaccgaga ggatgtacgt gcgcgacggc   480
gtgctgaagg gcgacgtcaa gatgaagctg ctgctggagg gcggcggcca ccaccgcgtt   540
gacttcaaga ccatctacag ggccaagaag gcggtgaagc tgcccgacta tcactttgtg   600
gaccaccgca tcgagatcct gaaccacgac aaggactaca caaggtgac cgtttacgag    660 atcgccgtgg cccgcaactc caccgacggc atggacgagc tgtacaagta a             711

<210> SEQ ID NO 13
<211> LENGTH: 712
<212> TYPE: DNA
<213> ORGANISM: Artificial Sequence
<220> FEATURE:
<223> OTHER INFORMATION: Reduced number of UU and/or UA dinucleotides

<400> SEQUENCE: 13
atggtgagca agggcgagga gaccacaatg ggcgtgatca agcccgacat gaagatcaag    60
ctgaagatgg agggcaacgt gaatggccac gccttcgtga tcgagggcga gggcgagggc   120
aagccctacg acggcaccaa caccatcaac ctggaggtga aggagggagc ccccctgccc   180
ttctcctacg acatcctgac caccgcgttc agctacggca cagggcctt caccaagtac   240 cccgacgaca tccccaacta cttcaagcag tccttccccg agggctacag ctgggagcgc   300
accatgacct tcgaggacaa gggcatcgtg aaggtgaagt ccgacatctc catggaggag   360
gactccttca tctacgagat ccacctcaag ggcgagaact ccccccaa cggcccgtg      420 atgcagaagg agaccaccgg ctgggacgcc tccaccgaga ggatgtacgt gcgcgacggc   480
gtgctgaagg gcgacgtcaa gatgaagctg ctgctggagg gcggcggcca ccaccgcgtg   540
gacttcaaga ccatctacag ggccaagaag gcggtgaagc tgcccgacta tcacttcgtg   600
gaccaccgca tcgagatcct gaaccacgac aaggactaca caaggtgac cgtgtacgag    660 atcgccgtgg cccgcaactc caccgacggc atggacgagc tgtacaagct ga            712

<210> SEQ ID NO 14
<211> LENGTH: 1368
<212> TYPE: DNA
<213> ORGANISM: Firefly

<400> SEQUENCE: 14
atggaagacg ccaaaaacat aaagaaaggc ccggcgccat tctatccgct ggaagatgga    60

```
accgctggag agcaactgca taaggctatg aagagatacg ccctggttcc tggaacaatt      120
gcttttacag atgcacatat cgaggtggac atcacttacg ctgagtactt cgaaatgtcc      180
gttcggttgg cagaagctat gaacgatatg ggctgaata caaatcacag aatcgtcgta      240
tgcagtgaaa actctcttca attcttatg ccggtgttgg gcgcgttatt tatcggagtt      300
gcagttgcgc ccgcgaacga catttataat gaacgtgaat tgctcaacag tatgggcatt      360
tcgcagccta ccgtggtgtt cgtttccaaa aaggggttgc aaaaaatttt gaacgtgcaa      420
aaaaagctcc caatcatcca aaaaattatt atcatggatt ctaaaacgga ttaccaggga      480
tttcagtcga tgtacacgtt cgtcacatct catctacctc ccggttttaa tgaatacgat      540
tttgtgccag agtccttcga tagggacaag acaattgcac tgatcatgaa ctcctctgga      600
tctactggtc tgcctaaagg tgtcgctctg cctcatagaa ctgcctgcgt gagattctcg      660
catgccagag atcctatttt tggcaatcaa atcattccgg atactgcgat tttaagtgtt      720
gttccattcc atcacggttt tggaatgttt actacactcg atatttgat atgtggattt      780 cgagtcgtct taatgtatag atttgaagaa gagctgtttc tgaggagcct tcaggattac      840
aagattcaaa gtgcgctgct ggtgccaacc ctattctcct tcttcgccaa aagcactctg      900
attgacaaat acgattatc taatttacac gaaattgctt ctggtggcgc tcccctctct      960
aaggaagtcg gggaagcggt tgccaagagg ttccatctgc caggtatcag gcaaggatat     1020
gggctcactg agactacatc agctattctg attacacccg aggggatga taaaccgggc     1080 gcggtcggta agttgttcc attttttgaa gcgaaggttg tggatctgga taccgggaaa     1140
acgctgggcg ttaatcaaag aggcgaactg tgtgtgagag gtcctatgat tatgtccggt     1200
tatgtaaaca atccggaagc gaccaacgcc ttgattgaca aggatggatg gctacattct     1260
ggagacatag cttactggga cgaagacgaa cacttcttca tcgttgaccg cctgaagtct     1320
ctgattaagt acaaaggcta tcaggtggct cccgctgaat tggaatcc                  1368

<210> SEQ ID NO 15
<211> LENGTH: 1650
<212> TYPE: DNA
<213> ORGANISM: Artificial Sequence
<220> FEATURE:
<223> OTHER INFORMATION: Reduced number of UU and/or UA dinucleotides

<400> SEQUENCE: 15
atggaagacg ccaaaaacat caagaaaggc ccggcgccat tctacccgct ggaagatgga       60
accgctggag agcaactgca caaggccatg aagagatacg ccctggtgcc tggaacaatc      120
gcgttcacag atgcacacat cgaggtggac atcacctacg ctgagtactt cgaaatgtcc      180
gtccggctgg cagaagccat gaacgatacg ggctgaaca caaatcacag aatcgtcgtg      240
tgcagtgaaa actctctgca attcttcatg ccggtgctgg gcgcgctgtt catcggagtg      300
gcagtcgcgc ccgcgaacga catctacaat gaacgtgaac tcctcaacag catgggcatc      360
tcgcagccca ccgtggtgtt cgtgtccaaa aaggggctgc aaaaaatcct gaacgtgcaa      420
aaaaagctcc caatcatcca aaaaatcatc atcatggaca gcaaaacgga ctaccaggga      480
ttccagtcga tgtacacgtt cgtcacatct catctgcctc ccggcttcaa tgaatacgac      540
ttcgtgccag agtccttcga cagggacaag acaatcgcac tgatcatgaa ctcctctgga      600
agcactggtc tgcccaaagg tgtcgctctg cctcacagaa ctgcctgcgt gagattctcg      660
catgccagag atcccatctt cggcaatcaa atcatcccgg acactgcgat cctgagtgtg      720
gtcccattcc atcacggctt cggaatgttc acgacactcg ataccctgat ctgtggattc      780
```

```
cgagtcgtcc tgatgtacag attcgaagaa gagctgttcc tgaggagcct ccaggactac      840
aagatccaaa gtgcgctgct ggtgccaacc ctgttctcct tcttcgccaa agcactctg       900 atcgacaaat acgatctcag caatctgcac gaaatcgcct ctggtggcgc tccctctcc       960 aaggaagtcg gggaagcggt cgccaagagg ttccatctgc agggatcag gcaaggatac      1020 gggctcactg agacgacatc agccatcctg atcacacccg aggggatga caaaccgggc      1080 gcggtcggga aagtggtccc attcttcgaa gcgaaggttg tggatctgga caccgggaaa      1140
acgctgggcg ttaatcaaag aggcgaactg tgtgtgagag gtcccatgat catgtccggc      1200
tacgtgaaca atccggaagc gaccaacgcc ctgatcgaca aggatggatg gctccactct      1260
ggagacatcg cgtactggga cgaagacgaa cacttcttca tcgtggaccg cctgaagtct      1320
ctgatcaagt acaaaggcta ccaggtggct cccgctgaac tcgaatccat cctgctccaa      1380
caccccaaca tcttcgacgc aggtgtcgca ggtctgcccg acgatgacgc cggtgaactg      1440
cccgccgccg tcgtggttct ggagcacgga aagacgatga cggaaaaaga gatcgtggac      1500
tacgtcgcca gtcaagtaac aaccgcgaaa aagctgcgcg gaggagttgt gttcgtggac      1560
gaagtgccga aggtctgac cggaaaaactc gacgcaagaa aaatcagaga gatcctcatc      1620
aaggccaaga agggcggaaa gatcgccgtg                                      1650
```

<210> SEQ ID NO 16
<211> LENGTH: 1656
<212> TYPE: DNA
<213> ORGANISM: Firefly

<400> SEQUENCE: 16

```
atggaagatg ccaaaaacat taagaagggc ccagcgccat tctacccact cgaagacggg       60
accgccggcg agcagctgca caaagccatg aagcgctacg ccctggtgcc cggcaccatc      120 gccttaccg acgcacatat cgaggtggac attacctacg ccgagtactt cgagatgagc       180
gttcggctgg cagaagctat gaagcgctat gggctgaata caaaccatcg gatcgtggtg      240
tgcagcgaga atagcttgca gttcttcatg cccgtgttgg gtgccctgtt catcggtgtg      300
gctgtggccc cagctaacga catctacaac gagcgcgagc tgctgaacag catgggcatc      360
agccagccca ccgtcgtatt cgtgagcaag aaagggctgc aaaagatcct caacgtgcaa      420
aagaagctac cgatcataca aaagatcatc atcatggata gcaagaccga ctaccagggc      480
ttccaaagca tgtacacctt cgtgacttcc catttgccac ccggcttcaa cgagtacgac      540
ttcgtgcccg agagcttcga ccgggacaaa accatcgccc tgatcatgaa cagtagtggc      600
agtaccggat tgcccaaggg cgtagcccta ccgcaccgca ccgcttgtgt ccgattcagt      660 catgccgcg accccatctt cggcaaccag atcatccccg acaccgctat cctcagcgtg      720
gtgccatttc accacggctt cggcatgttc accacgctgg gctacttgat ctgcggcttt      780
cgggtcgtgc tcatgtaccg cttcgaggag gagctattct tgcgcagctt gcaagactat      840
aagattcaat ctgccctgct ggtgccacac ctatttagct tcttcgctaa gagcactctc      900
atcgacaagt acgacctaag caacttgcac gagatcgcca gcggcggggc gccgctcagc      960
aaggaggtag gtgaggccgt ggccaaacgc ttccacctac aggcatccg ccagggctac     1020 ggcctgacag aaacaaccag cgccattctg atcaccccg aaggggacga caagcctggc     1080
gcagtaggca aggtggtgcc cttcttcgag gctaaggtgg tggacttgga caccggtaag     1140
acactgggtg tgaaccagcg cggcgagctg tgcgtccgtg gccccatgat catgagcggc     1200
```

```
tacgttaaca accccgaggc tacaaacgct ctcatcgaca aggacggctg gctgcacagc    1260
ggcgacatcg cctactggga cgaggacgag cacttcttca tcgtggaccg gctgaagagc    1320
ctgatcaaat acaagggcta ccaggtagcc ccagccgaac tggagagcat cctgctgcaa    1380 cacccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg tggtgttgt gttcgtggac    1560 gaggtgccta aaggactgac cggcaagttg gacgcccgca agatccgcga gattctcatt    1620
aaggccaaga agggcggcaa gatcgccgtg taataa                              1656
```

<210> SEQ ID NO 17
<211> LENGTH: 1653
<212> TYPE: DNA
<213> ORGANISM: Artificial Sequence
<220> FEATURE:
<223> OTHER INFORMATION: Reduced number of UU and/or UA dinucleotides

<400> SEQUENCE: 17

```
atggaagatg ccaaaaacat caagaagggc ccagcgccat tctacccact cgaagacggg     60
accgcaggcg agcagctgca caaagccatg aagcgctacg ccctggtgcc cggcaccatc    120
gccttcaccg acgcacacat cgaggtggac atcacctacg ccgagtactt cgagatgagc    180
gtgcggctgg cagaagccat gaagcgctac gggctgaaca caaaccatcg gatcgtggtg    240
tgcagcgaga cagcctgca gttcttcatg cccgtgctgg gtgccctgtt catcggtgtg    300
gctgtggccc cagccaacga catctacaac gagcgcgagc tgctgaacag catgggcatc    360
agccagccca ccgtcgtgtt cgtgagcaag aaagggctgc aaaagatcct caacgtgcaa    420
aagaagctgc cgatcatcca aaagatcatc atcatggaca gcaagaccga ctaccagggc    480
ttccaaagca tgtacaccct cgtgacctcc cacctgccac ccggcttcaa cgagtacgac    540
ttcgtgcccg agagcttcga ccgggacaaa accatcgccc tgatcatgaa cagcagtggc    600
agcaccggac tgcccaaggg cgtggcactg ccgcaccgca ccgcctgtgt ccgattcagt    660
catgcacgcg accccatctt cggcaaccag atcatccccg acaccgccat cctcagcgtg    720
gtgccattcc accacggctt cggcatgttc accacgctgg gctactggat ctgcggcttc    780
cgggtcgtgc tcatgtaccg cttcgaggag gagctgttcc tgcgcagcct gcaagactac    840
aagatccaat ctgccctgct ggtgcccaca ctgttcagct tcttcgccaa gagcactctc    900
atcgacaagt acgacctgag caacctgcac gagatcgcca cggcggagc gccgctcagc    960 aaggaggtgg gtgaggccgt ggccaaacgc ttccacctgc aggcatccg ccagggctac    1020 ggcctgacag aaacaaccag cgccattctg atcacccccg aagggagcga caagcctggc    1080
gcagtgggca aggtggtgcc cttcttcgag gccaaggtgg tggacctgga caccggcaag    1140
acactgggtg tgaaccagcg cggcgagctg tgcgtccgtg gccccatgat catgagcggc    1200
tacgtgaaca ccccgaggc cacaaacgct ctcatcgaca aggacggctg gctgcacagc    1260
ggcgacatcg cctactggga cgaggacgag cacttcttca tcgtggaccg gctgaagagc    1320
ctgatcaaat acaagggcta ccaggtgccc ccagccgaac tggagagcat cctgctgcaa    1380 cacccccaaca tcttcgacgc cggagtcgcc ggactgccag acgacgatgc cggcgagctg    1440
cccgcagcag tcgtcgtgct ggaacacggt aaaaccatga ccgagaagga gatcgtggac    1500
tacgtggcca gccaggtgac aaccgccaag aagctgcgcg tggtgtggt gttcgtggac    1560 gaggtgccca aaggactgac cggcaagctg gacgcccgca agatccgcga gatcctcatc    1620
```
aaggccaaga agggcggcaa gatcgccgtg tga                                    1653

<210> SEQ ID NO 18
<211> LENGTH: 697
<212> TYPE: DNA
<213> ORGANISM: Puntellina plumate

<400> SEQUENCE: 18
atggagagcg acgagagcgg cctgcccgcc atggagatcg agtgccgcat caccggcacc    60
ctgaacggcg tggagttcga gctggtgggc ggcggagagg gcaccccccga gcagggccgc   120 atgaccaaca agatgaagag caccaaaggc gccctgacct tcagcccta cctgctgagc    180 cacgtgatgg gctacggctt ctaccacttc ggcacctacc ccagcggcta cgagaacccc   240
ttcctgcacg ccatcaacaa cggcggctac accaacaccc gcatcgagaa gtacgaggac   300
ggcggcgtgc tgcacgtgag cttcagctac cgctacgagg ccggccgcgt gatcggcgac   360
ttcaaggtga tgggcaccgg cttccccgag acagcgtga tcttcaccga caagatcatc    420
cgcagcaacg ccaccgtgga gcacctgcac cccatgggcg ataacgatct ggatggcagc   480
ttcacccgca ccttcagcct gcgcgacggc ggctactaca gctccgtggt ggacagccac   540
atgcacttca gagcgccat ccaccccagc atcctgcaga acggggccc catgttcgcc    600 ttccgccgcg tggaggagga tcacagcaac accgagctgg gcatcgtgga gtaccagcac   660
gccttcaaga ccccggatgc agatgccggt gaagaaa                            697

<210> SEQ ID NO 19
<211> LENGTH: 700
<212> TYPE: DNA
<213> ORGANISM: Artificial Sequence
<220> FEATURE:
<223> OTHER INFORMATION: Reduced number of UU and/or UA dinucleotides

<400> SEQUENCE: 19
atggagagcg acgagagcgg cctgcccgcc atggagatcg agtgccgcat caccggcacc    60
ctgaacggcg tggagttcga gctggtgggc ggcggagagg gcaccccccga gcagggccgc   120 atgaccaaca agatgaagag caccaaaggc gccctgacct tcagcccta cctgctgagc    180 cacgtgatgg gctacggctt ctaccacttc ggcacctacc ccagcggcta cgagaacccc   240
ttcctgcacg ccatcaacaa cggcggctac accaacaccc gcatcgagaa gtacgaggac   300
ggcggcgtgc tgcacgtgag cttcagctac cgctacgagg ccggccgcgt gatcggcgac   360
ttcaaggtga tgggcaccgg cttccccgag acagcgtga tcttcaccga caagatcatc    420
cgcagcaacg ccaccgtgga gcacctgcac cccatgggcg acaacgacct ggatggcagc   480
ttcacccgca ccttcagcct gcgcgacggc ggctactaca gctccgtggt ggacagccac   540
atgcacttca gagcgccat ccaccccagc atcctgcaga acggggccc catgttcgcc    600 ttccgccgcg tggaggagga tcacagcaac accgagctgg gcatcgtgga gtaccagcac   660
gccttcaaga ccccggatgc agatgccggt gaagaactga                         700

<210> SEQ ID NO 20
<211> LENGTH: 698
<212> TYPE: DNA
<213> ORGANISM: Discosoma species

<400> SEQUENCE: 20
atgagcgagc tgatcaagga gaacatgcac atgaagctgt acatggaggg caccgtgaac    60

```
aaccaccact tcaagtgcac atccgagggc gaaggcaagc cctacgaggg cacccagacc    120
atgaagatca aggtggtcga gggcggccct ctccccttcg ccttcgacat cctggctacc    180
agcttcatgt acggcagcaa agccttcatc aaccacaccc agggcatccc cgacttcttt    240
aagcagtcct ccctgagggg cttcacatgg gagagaatca ccacatacga agacgggggc    300
gtgctgaccg ctacccagga caccagcttc agaacggct  gcatcatcta caacgtcaag    360
atcaacgggg tgaacttccc atccaacggc cctgtgatgc agaagaaaac acgcggctgg    420
gaggccaaca ccgagatgct gtaccccgct gacggcggcc tgagaggcca cagccagatg    480
gccctgaagc tcgtgggcgg gggctacctg cactgctcct tcaagaccac atacagatcc    540
aagaaacccg ctaagaacct caagatgccc ggcttccact tcgtggacca cagactggaa    600
agaatcaagg aggccgacaa agagacctac gtcgagcagc acgagatggc tgtggccaag    660
tactgcgacc tccctagcaa actggggcac agagatga                            698
```

<210> SEQ ID NO 21
<211> LENGTH: 694
<212> TYPE: DNA
<213> ORGANISM: Artificial Sequence
<220> FEATURE:
<223> OTHER INFORMATION: Reduced number of UU and/or UA dinucleotides

<400> SEQUENCE: 21

```
atgagcgagc tgatcaagga gaacatgcac atgaagctgt acatggaggg caccgtgaac     60
aaccaccact tcaagtgcac atccgagggc gaaggcaagc cctacgaggg cacccagacc    120
atgaagatca aggtggtcga gggcggccca ctccccttcg ccttcgacat cctggccacc    180
agcttcatgt acggcagcaa agccttcatc aaccacaccc agggcatccc cgacttcttc    240
aagcagtcct ccctgagggg cttcacatgg gagagaatca ccacatacga agacgggggc    300
gtgctgaccg ccacccagga caccagcttc agaacggct  gcatcatcta caacgtcaag    360
atcaacgggg tgaacttccc atccaacggc cctgtgatgc agaagaaaac acgcggctgg    420
gaggccaaca ccgagatgct gtaccccgct gacggcggcc tgagaggcca cagccagatg    480
gccctgaagc tcgtgggcgg gggctacctg cactgctcct tcaagaccac atacagatcc    540
aagaaacccg ccaagaacct caagatgccc ggcttccact tcgtggacca cagactggaa    600
agaatcaagg aggccgacaa agagacctac gtcgagcagc acgagatggc tgtggccaag    660
tactgcgacc tcccaagcaa actggggcac agac                                694
```

<210> SEQ ID NO 22
<211> LENGTH: 681
<212> TYPE: DNA
<213> ORGANISM: Hepatitis B virus

<400> SEQUENCE: 22

```
atggagaaca caacatcagg attcctagga cccctgctcg tgttacaggc ggggttttc     60 ttgttgacaa gaatcctcac aataccacag agtctagact cgtggtggac ttctctcaat    120
tttctagggg gagcacccac gtgtcctggc caaattcgc  agtccccaac ctccaatcac    180
tcaccaacct cttgtcctcc aatttgtcct ggctatcgct ggatgtgtct gcggcgtttt    240
atcatattcc tcttcatcct gctgctatgc ctcatcttct tgttggttct tctggactac    300
caaggtatgt tgcccgtttg tcctctactt ccaggaacat caactaccag cacgggacca    360
tgcaagacct gcacgattcc tgctcaagga acctctatgt ttccctcctg ttgctgtaca    420
aaaccttcgg acggaaactg cacttgtatt cccatcccat catcctgggc tttcgcaaga    480
```

```
ttcctatggg agtgggcctc agtccgtttc tcctggctca gtttactagt gccatttgtt      540
cagtggttcg tagggctttc ccccactgtt tggctttcag ttatatggat gatgtggtat      600
tgggggccaa gtctgtacaa catcttgagt ccctttttac ctctattacc aattttcttt      660
tgtctttggg tatacatttg a                                                681

<210> SEQ ID NO 23
<211> LENGTH: 681
<212> TYPE: DNA
<213> ORGANISM: Artificial Sequence
<220> FEATURE:
<223> OTHER INFORMATION: Reduced number of UU and/or UA dinucleotides

<400> SEQUENCE: 23
atggagaaca ccaccagcgg cttcctgggc cctctgctgg tgctgcaggc cggcttcttc       60
ctgctgaccc gcatcctgac catccccag agcctggaca gctggtggac cagcctgaac      120
ttcctgggcg gagccccaac ctgtcccggc ccaacagcc agagcccac cagcaaccac       180 agcccaacca gctgcccacc catctgtccc ggctaccggt ggatgtgcct gcggcggttc      240
atcatcttcc tgttcatcct gctgctgtgc ctgatcttcc tcctggtgct cctggactac      300
cagggcatgc tgcccgtgtg tcctctgctg cctggcacca gcaccacctc caccggcccc      360
tgcaagacct gcacaatccc cgcccaggga accagcatgt tcccaagctg ctgctgcacc      420
aagcccagcg acggcaactg cacctgcatc cccatcccaa gcagctgggc cttcgccaga      480
ttcctgtggg agtgggcctc cgtgagattc agctggctgt cactgctggt gcccttcgtg      540
cagtggttcg tgggcctgag cccaacagtg tggctgagcg tgatctggat gatgtggtac      600
tggggaccca gcctgtacaa catcctgagc cccttcctgc cctgctgcc catcttcttc      660 tgcctgtggg tgtacatctg a                                                681

<210> SEQ ID NO 24
<211> LENGTH: 681
<212> TYPE: DNA
<213> ORGANISM: Artificial Sequence
<220> FEATURE:
<223> OTHER INFORMATION: Reduced number of UU and/or UA dinucleotides

<400> SEQUENCE: 24
atggagaaca caacatcagg attcctcgga cccctgctcg tgctgcaggc ggggttcttc       60
ctgctcacaa gaatcctcac aatcccacag agtctggact cgtggtggac gtctctcaac      120
ttcctcgggg gagcacccac gtgtcctggc ccaaactcgc agtccccaac ctccaatcac      180
tcaccaacct cgtgtcctcc aatctgtcct ggctaccgct ggatgtgtct gcggcgcttc      240
atcatcttcc tcttcatcct gctgctgtgc ctcatcttcc tgctcgtcct cctggactac      300
caagggatgc tgcccgtctg tcctctgctg ccaggaacat caaccaccag cacgggacca      360
tgcaagacct gcacgatccc tgctcaagga accagcatgt tcccctcctg ctgctgcaca      420
aaaccatcgg acggaaactg cacctgcatc cccatcccat catcctgggc cttcgcaaga      480
ttcctctggg agtgggcctc agtccggttc tcctggctca gtctcctggt gccattcgtg      540
cagtggttcg tcgggctgtc ccccactgtg tggctgtcag tgatctggat gatgtggtac      600
tgggggccaa gtctgtacaa catcctcagt cccttcctgc ctctgctgcc aatcttcttc      660
tgtctgtggg tgtacatctg a                                                681

<210> SEQ ID NO 25
```

<211> LENGTH: 567
<212> TYPE: DNA
<213> ORGANISM: Homo sapiens

<400> SEQUENCE: 25

| | | | | | |
|---|---|---|---|---|---|
| atggccttga | cctttgcttt | actggtggcc | ctcctggtgc | tcagctgcaa | gtcaagctgc | 60 |
| tctgtgggct | gtgatctgcc | tcaaacccac | agcctgggta | gcaggaggac | cttgatgctc | 120 |
| ctggcacaga | tgaggagaat | ctctcttttc | tcctgcttga | aggacagaca | tgactttgga | 180 |
| tttccccagg | aggagtttgg | caaccagttc | caaaaggctg | aaaccatccc | tgtcctccat | 240 |
| gagatgatcc | agcagatctt | caatctcttc | agcacaaagg | actcatctgc | tgcttgggat | 300 |
| gagaccctcc | tagacaaatt | ctacactgaa | ctctaccagc | agctgaatga | cctggaagcc | 360 |
| tgtgtgatac | aggggtggg | ggtgacagag | actcccctga | tgaaggagga | ctccattctg | 420 |
| gctgtgagga | aatacttcca | aagaatcact | ctctatctga | aagagaagaa | atacagccct | 480 |
| tgtgcctggg | aggttgtcag | agcagaaatc | atgagatctt | tttctttgtc | aacaaacttg | 540 |
| caagaaagtt | taagaagtaa | ggaatga | | | | 567 |

<210> SEQ ID NO 26
<211> LENGTH: 567
<212> TYPE: DNA
<213> ORGANISM: Artificial Sequence
<220> FEATURE:
<223> OTHER INFORMATION: Reduced number of UU and/or UA dinucleotides

<400> SEQUENCE: 26

| | | | | | |
|---|---|---|---|---|---|
| atggccctga | ccttcgccct | gctggtggct | ctgctggtgc | tgagctgcaa | gagcagctgc | 60 |
| agcgtgggct | gcgatctgcc | tcagacccac | agcctgggca | gcagacggac | actgatgctg | 120 |
| ctggcccaga | tgcggcggat | cagcctgttc | agctgcctga | aggaccggca | cgacttcggc | 180 |
| ttccccagg | aagagttcgg | caaccagttc | cagaaggccg | agacaatccc | cgtgctgcac | 240 |
| gagatgatcc | agcagatctt | caacctgttc | agcaccaagg | acagcagcgc | cgcctgggac | 300 |
| gagacactgc | tggacaagtt | ctacaccgag | ctgtaccagc | agctgaacga | cctggaagcc | 360 |
| tgcgtgatcc | agggcgtggg | cgtgaccgag | acacccctga | tgaaggaaga | cagcatcctg | 420 |
| gccgtgcgga | agtacttcca | gcggatcacc | ctgtacctga | agagaagaa | gtacagcccc | 480 |
| tgcgcctggg | aagtggtccg | ggccgagatc | atgcggagct | tcagcctgag | caccaacctg | 540 |
| caggaaagcc | tgcggagcaa | agagtga | | | | 567 |

<210> SEQ ID NO 27
<211> LENGTH: 612
<212> TYPE: DNA
<213> ORGANISM: Homo sapiens

<400> SEQUENCE: 27

| | | | | | |
|---|---|---|---|---|---|
| atggctggac | ctgccaccca | gagccccatg | aagctgatgg | ccctgcagct | gctgctgtgg | 60 |
| cacagtgcac | tctggacagt | gcaggaagcc | accccctgg | gccctgccag | ctccctgccc | 120 |
| cagagcttcc | tgctcaagtg | cttagagcaa | gtgaggaaga | tccagggcga | tggcgcagcg | 180 |
| ctccaggaga | agctgtgtgc | cacctacaag | ctgtgccacc | ccgaggagct | ggtgctgctc | 240 |
| ggacactctc | tgggcatccc | ctgggctccc | ctgagcagct | gcccagcca | ggccctgcag | 300 |
| ctggcaggct | gcttgagcca | actccatagc | ggccttttcc | tctaccaggg | gctcctgcag | 360 |
| gccctggaag | ggatctcccc | cgagttgggt | cccaccttgg | acacactgca | gctggacgtc | 420 |
| gccgactttg | ccaccaccat | ctggcagcag | atggaagaac | tgggaatggc | ccctgccctg | 480 |

```
cagcccaccc agggtgccat gccggccttc gcctctgctt tccagcgccg ggcaggaggg    540
gtcctagttg cctcccatct gcagagcttc ctggaggtgt cgtaccgcgt tctacgccac    600
cttgcccagc cc                                                        612

<210> SEQ ID NO 28
<211> LENGTH: 612
<212> TYPE: DNA
<213> ORGANISM: Artificial Sequence
<220> FEATURE:
<223> OTHER INFORMATION: Reduced number of UU and/or UA dinucleotides

<400> SEQUENCE: 28
atggctggac ctgccaccca gagccccatg aagctgatgg ccctgcagct gctgctgtgg    60
cacagtgcac tctggacagt gcaggaagcc accccctgg gccctgccag ctccctgccc     120
cagagcttcc tgctcaagtg cctggagcaa gtgaggaaga tccagggcga tggcgcagcg    180
ctccaggaga agctgtgtgc cacctacaag ctgtgccacc ccgaggagct ggtgctgctc    240
ggacactctc tgggcatccc ctgggctccc ctgagcagct gccccagcca ggccctgcag    300
ctggcaggct gcctgagcca actccacagc ggcctcttcc tctaccaggg gctcctgcag    360
gccctggaag ggatctcccc cgagctgggt cccaccctgg acacactgca gctggacgtc    420
gccgacttcg ccaccaccat ctggcagcag atggaagaac tgggaatggc ccctgccctg    480
cagcccaccc agggtgccat gccggccttc gcctctgcct tccagcgccg ggcaggaggg    540
gtcctggtgg cctcccatct gcagagcttc ctggaggtgt cgtaccgcgt gctccgccac    600
ctcgcccagc cc                                                        612

<210> SEQ ID NO 29
<211> LENGTH: 123
<212> TYPE: DNA
<213> ORGANISM: Mus musculus

<400> SEQUENCE: 29
cagagccatg gcttcccgcc ggaggtggag gagcaggatg atggcacgct gcccatgtct    60
tgtgcccagg agagcgggat ggaccgtcac cctgcagcct gtgcttctgc taggatcaat    120
gtg                                                                  123

<210> SEQ ID NO 30
<211> LENGTH: 125
<212> TYPE: DNA
<213> ORGANISM: Artificial Sequence
<220> FEATURE:
<223> OTHER INFORMATION: Reduced number of UU and/or UA dinucleotides

<400> SEQUENCE: 30
agtctcacgg cttcccaccc gaggtcgagg agcaggatga tggcacactg cccatgagct    60
gtgctcagga gtctggcatg gacagacacc ccgctgcctg tgccagtgcc aggatcaatg    120
tgtga                                                                125

<210> SEQ ID NO 31
<211> LENGTH: 806
<212> TYPE: DNA
<213> ORGANISM: Artificial Sequence
<220> FEATURE:
<223> OTHER INFORMATION: MODC destabilised and UU/UA reduced sequence of
      Montastrea cavernosa GFP (green fluorescent protein)

<400> SEQUENCE: 31
```

```
atgggcgtga tcaagcccga catgaagatc aagctgcgga tggagggcgc cgtgaacggc      60
cacaaattcg tgatcgaggg cgacgggaaa ggcaagccct cgagggcaa gcagacgatg      120 gacctgaccg tgatcgaggg cgccccctg cccttcgcct acgacatcct gaccaccgtg      180
ttcgactacg gcaaccgtgt cttcgccaag taccccaagg acatccctga ctacttcaag      240
cagaccttcc ccgagggcta ctcgtgggag cgaagcatga catacgagga ccagggaatc      300
tgcatcgcga caaacgacat caccatgatg aagggtgtgg acgactgctt cgtgtacaaa      360
atccgcttcg acgggtcaa cttccctgcc aatggcccgg tgatgcagcg caagaccctg      420
aagtgggagc ccagcaccga aagatgtac gtgcgggacg cgtcctgaa gggcgatgtg       480 aacatggcac tgctcctgga gggaggcggc cactaccgct gcgacttcaa gaccacctac      540
aaagccaaga aggtggtgca gctgcccgac taccacttcg tggaccaccg catcgagatc      600
gtgagccacg acaaggacta caacaaagtc aagctgtacg agcacgccga agcccacagc      660
ggactgcccc gccaggccgg cagtctcacg gcttcccacc cgaggtcgag gagcaggatg      720
atggcacact gcccatgagc tgtgctcagg agtctggcat ggacagacac cccgctgcct      780
gtgccagtgc caggatcaat gtgtga                                          806

<210> SEQ ID NO 32
<211> LENGTH: 834
<212> TYPE: DNA
<213> ORGANISM: Artificial Sequence
<220> FEATURE:
<223> OTHER INFORMATION: MODC destabilised and UU/UA reduced sequence of
      Clavularia species GFP

<400> SEQUENCE: 32
atggtgagca agggcgagga gaccacaatg ggcgtgatca gcccgacat gaagatcaag       60 ctgaagatgg agggcaacgt gaatggccac gccttcgtga tcgagggcga gggcgagggc      120
aagccctacg acggcaccaa caccatcaac ctggaggtga aggagggagc cccctgccc      180 ttctcctacg acatcctgac caccgcgttc agctacggca cagggcctt caccaagtac      240 cccgacgaca tccccaacta cttcaagcag tccttcccg agggctacag ctgggagcgc      300
accatgacct tcgaggacaa gggcatcgtg aaggtgaagt ccgacatctc catggaggag      360
gactccttca tctacgagat ccacctcaag ggcgagaact cccccccaa cggccccgtg      420 atgcagaagg agaccaccgg ctgggacgcc tccaccgaga ggatgtacgt gcgcgacggc      480
gtgctgaagg gcgacgtcaa gatgaagctg ctgctggagg gcggcggcca ccaccgcgtg      540
gacttcaaga ccatctacag ggccaagaag gcggtgaagc tgcccgacta tcacttcgtg      600
gaccaccgca tcgagatcct gaaccacgac aaggactaca caaggtgac cgtgtacgag      660 atcgccgtgg cccgcaactc caccgacggc atggacgagc tgtacaagca gtctcacggc      720
ttcccacccg aggtcgagga gcaggatgat ggcacactgc ccatgagctg tgctcaggag      780
tctggcatgg acagacaccc cgctgcctgt gccagtgcca ggatcaatgt gtga           834

<210> SEQ ID NO 33
<211> LENGTH: 1775
<212> TYPE: DNA
<213> ORGANISM: Artificial Sequence
<220> FEATURE:
<223> OTHER INFORMATION: MODC destabilised and UU/UA reduced sequence of
      firefly luciferase

<400> SEQUENCE: 33
```

```
atggaagacg ccaaaaacat caagaaaggc ccggcgccat tctacccgct ggaagatgga      60
accgctggag agcaactgca caaggccatg aagagatacg ccctggtgcc tggaacaatc     120
gcgttcacag atgcacacat cgaggtggac atcacctacg ctgagtactt cgaaatgtcc     180
gtccggctgg cagaagccat gaaacgatac gggctgaaca caaatcacag aatcgtcgtg     240
tgcagtgaaa actctctgca attcttcatg ccggtgctgg gcgcgctgtt catcggagtg     300
gcagtcgcgc ccgcgaacga catctacaat gaacgtgaac tcctcaacag catgggcatc     360
tcgcagccca ccgtggtgtt cgtgtccaaa aaggggctgc aaaaaatcct gaacgtgcaa     420
aaaaagctcc caatcatcca aaaaatcatc atcatggaca gcaaaacgga ctaccaggga     480
ttccagtcga tgtacacgtt cgtcacatct catctgcctc ccggcttcaa tgaatacgac     540
ttcgtgccag agtccttcga cagggacaag acaatcgcac tgatcatgaa ctcctctgga     600
agcactggtc tgcccaaagg tgtcgctctg cctcacagaa ctgcctgcgt gagattctcg     660
catgccagag atcccatctt cggcaatcaa atcatcccgg acactgcgat cctgagtgtg     720
gtcccattcc atcacggctt cggaatgttc acgacactcg ataccgat ctgtggattc       780
cgagtcgtcc tgatgtacag attcgaagaa gagctgttcc tgaggagcct ccaggactac     840
aagatccaaa gtgcgctgct ggtgccaacc ctgttctcct tcttcgccaa agcactctg      900
atcgacaaat acgatctcag caatctgcac gaaatcgcct ctggtggcgc tcccctctcc     960
aaggaagtcg gggaagcggt cgccaagagg ttccatctgc cagggatcag gcaaggatac    1020
gggctcactg agacgacatc agccatcctg atcacacccg aggggatga caaaccgggc    1080
gcggtcggga aagtggtccc attcttcgaa gcgaaggttg tggatctgga caccgggaaa    1140
acgctgggcg ttaatcaaag aggcgaactg tgtgtgagag gtcccatgat catgtccggc    1200
tacgtgaaca atccggaagc gaccaacgcc ctgatcgaca aggatggatg gctccactct    1260
ggagacatcg cgtactggga cgaagacgaa cacttcttca tcgtggaccg cctgaagtct    1320
ctgatcaagt acaaaggcta ccaggtggct cccgctgaac tcgaatccat cctgctccaa    1380
caccccaaca tcttcgacgc aggtgtcgca ggtctgcccg acgatgacgc cggtgaactg    1440
cccgccgccg tcgtggttct ggagcacgga aagacgatga cggaaaaaga gatcgtggac    1500
tacgtcgcca gtcaagtaac aaccgcgaaa aagctgcgcg gaggagttgt gttcgtggac    1560
gaagtgccga aggtctgac cggaaaaactc gacgcaagaa aaatcagaga gatcctcatc    1620
aaggccaaga agggcggaaa gatcgccgtg agtctcacgg cttcccaccc gaggtcgagg    1680
agcaggatga tggcacactg cccatgagct gtgctcagga gtctggcatg gacagacacc    1740
ccgctgcctg tgccagtgcc aggatcaatg tgtga                               1775
```

<210> SEQ ID NO 34
<211> LENGTH: 1775
<212> TYPE: DNA
<213> ORGANISM: Artificial Sequence
<220> FEATURE:
<223> OTHER INFORMATION: MODC destabilised and UU/UA reduced sequence of
      firefly luciferase

<400> SEQUENCE: 34

```
atggaagatg ccaaaaacat caagaagggc ccagcgccat tctacccact cgaagacggg      60
accgcaggcg agcagctgca caaagccatg aagcgctacg ccctggtgcc cggcaccatc     120
gccttcaccg acgcacacat cgaggtggac atcacctacg ccgagtactt cgagatgagc     180
gtgcggctgg cagaagccat gaagcgctac gggctgaaca caaaccatcg gatcgtggtg     240
```

```
tgcagcgaga acagcctgca gttcttcatg cccgtgctgg gtgccctgtt catcggtgtg      300
gctgtggccc cagccaacga catctacaac gagcgcgagc tgctgaacag catgggcatc      360
agccagccca ccgtcgtgtt cgtgagcaag aaagggctgc aaaagatcct caacgtgcaa      420
aagaagctgc cgatcatcca aaagatcatc atcatggaca gcaagaccga ctaccagggc      480
ttccaaagca tgtacacctt cgtgacctcc cacctgccac ccggcttcaa cgagtacgac      540
ttcgtgcccg agagcttcga ccgggacaaa accatcgccc tgatcatgaa cagcagtggc      600
agcaccggac tgcccaaggg cgtggcactg ccgcaccgca ccgcctgtgt ccgattcagt      660
catgcacgcg accccatctt cggcaaccag atcatccccg acaccgccat cctcagcgtg      720
gtgccattcc accacggctt cggcatgttc accacgctgg gctactggat ctgcggcttc      780
cgggtcgtgc tcatgtaccg cttcgaggag gagctgttcc tgcgcagcct gcaagactac      840
aagatccaat ctgccctgct ggtgcccaca ctgttcagct tcttcgccaa gagcactctc      900
atcgacaagt acgacctgag caacctgcac gagatcgcca cggcggagc gccgctcagc       960 aaggaggtgg tgaggccgt ggccaaacgc ttccacctgc aggcatccg ccagggctac       1020 ggcctgacag aaacaaccag cgccattctg atcacccccg aagggacga caagcctggc      1080 gcagtgggca aggtggtgcc cttcttcgag gccaaggtgg tggacctgga caccggcaag      1140
acactgggtg tgaaccagcg cggcgagctg tgcgtccgtg gccccatgat catgagcggc      1200
tacgtgaaca cccccgaggc cacaaacgct ctcatcgaca aggacggctg gctgcacagc      1260
ggcgacatcg cctactggga cgaggacgag cacttcttca tcgtggaccg gctgaagagc      1320
ctgatcaaat acaagggcta ccaggtggcc ccagccgaac tggagagcat cctgctgcaa      1380
caccccaaca tcttcgacgc cggagtcgcc ggactgccag acgacgatgc cggcgagctg      1440
cccgcagcag tcgtcgtgct ggaacacggc aaaaccatga ccgagaagga gatcgtggac      1500
tacgtggcca gccaggtgac aaccgccaag aagctgcgcg tggtgtggt gttcgtggac      1560 gaggtgccca aaggactgac cggcaagctg gacgcccgca agatccgcga gatcctcatc      1620
aaggccaaga agggcggcaa gatcgccgtg agtctcacgg cttcccaccc gaggtcgagg      1680
agcaggatga tggcacactg cccatgagct gtgctcagga gtctggcatg gacagacacc      1740
ccgctgcctg tgccagtgcc aggatcaatg tgtga                                 1775
```

<210> SEQ ID NO 35
<211> LENGTH: 822
<212> TYPE: DNA
<213> ORGANISM: Artificial Sequence
<220> FEATURE:
<223> OTHER INFORMATION: MODC destabilised and UU/UA reduced sequence of
      Puntellina plumate GFP

<400> SEQUENCE: 35

```
atggagagcg acgagagcgg cctgcccgcc atggagatcg agtgccgcat caccggcacc       60
ctgaacggct ggagttcga gctggtgggc ggcggagagg gcaccccga gcagggccgc       120 atgaccaaca agatgaagag caccaaaggc gccctgacct tcagccccta cctgctgagc      180
cacgtgatgg gctacggctt ctaccacttc ggcacctacc ccagcggcta cgagaacccc      240
ttcctgcacg ccatcaacaa cggcggctac accaacaccc gcatcgagaa gtacgaggac      300
ggcggcgtgc tgcacgtgag cttcagctac cgctacgagg ccggccgcgt gatcggcgac      360
ttcaaggtga tgggcaccgg cttccccgag gacagcgtga tcttcaccga caagatcatc      420
cgcagcaacg ccaccgtgga gcacctgcac cccatgggcg acaacgacct ggatggcagc      480
```

```
ttcacccgca ccttcagcct gcgcgacggc ggctactaca gctccgtggt ggacagccac      540
atgcacttca agagcgccat ccaccccagc atcctgcaga acggggggccc catgttcgcc     600 ttccgccgcg tggaggagga tcacagcaac accgagctgg gcatcgtgga gtaccagcac     660
gccttcaaga ccccggatgc agatgccggt gaagaacagt ctcacggctt cccacccgag     720
gtcgaggagc aggatgatgg cacactgccc atgagctgtg ctcaggagtc tggcatggac     780
agacaccccg ctgcctgtgc cagtgccagg atcaatgtgt ga                        822

<210> SEQ ID NO 36
<211> LENGTH: 819
<212> TYPE: DNA
<213> ORGANISM: Artificial Sequence
<220> FEATURE:
<223> OTHER INFORMATION: MODC destabilised and UU/UA reduced sequence of
      Discosoma RFP (red fluorescent protein)

<400> SEQUENCE: 36
atgagcgagc tgatcaagga gaacatgcac atgaagctgt acatggaggg caccgtgaac      60
aaccaccact tcaagtgcac atccgagggc gaaggcaagc cctacgaggg cacccagacc     120
atgaagatca aggtggtcga gggcggccca ctccccttcg ccttcgacat cctggccacc     180
agcttcatgt acggcagcaa agccttcatc aaccacaccc agggcatccc cgacttcttc     240
aagcagtcct ccctgaggg cttcacatgg gagagaatca ccacatacga agacggggc      300 gtgctgaccg ccacccagga caccagcttc cagaacggct gcatcatcta caacgtcaag     360
atcaacgggg tgaacttccc atccaacggc cctgtgatgc agaagaaaac acgcggctgg     420
gaggccaaca ccgagatgct gtaccccgct gacggcggcc tgagaggcca cagccagatg     480
gccctgaagc tcgtgggcgg gggctacctg cactgctcct tcaagaccac atacagatcc     540
aagaaacccg ccaagaacct caagatgccc ggcttccact tcgtggacca cagactggaa     600
agaatcaagg aggccgacaa agagacctac gtcgagcagc acgagatggc tgtggccaag     660
tactgcgacc tcccaagcaa actggggcac agacagtctc acggcttccc acccgaggtc     720
gaggagcagg atgatggcac actgcccatg agctgtgctc aggagtctgg catggacaga     780
caccccgctg cctgtgccag tgccaggatc aatgtgtga                           819
```